United States Patent
Scheib

(10) Patent No.: US 10,463,885 B2
(45) Date of Patent: Nov. 5, 2019

(54) DOSIMETRIC END-TO-END VERIFICATION DEVICES, SYSTEMS, AND METHODS

(71) Applicant: VARIAN MEDICAL SYSTEMS INTERNATIONAL AG, Zug (CH)

(72) Inventor: Stefan Scheib, Waedenswil (CH)

(73) Assignee: VARIAN MEDICAL SYSTEMS INTERNATIONAL AG, Zug (CH)

(*) Notice: Subject to any disclaimer, the term of this patent is extended or adjusted under 35 U.S.C. 154(b) by 0 days.

(21) Appl. No.: 15/365,533

(22) Filed: Nov. 30, 2016

(65) Prior Publication Data

US 2017/0080254 A1 Mar. 23, 2017

Related U.S. Application Data

(63) Continuation of application No. 14/038,595, filed on Sep. 26, 2013, now Pat. No. 9,643,029.

(51) Int. Cl.
*A61N 5/10* (2006.01)

(52) U.S. Cl.
CPC ......... *A61N 5/1075* (2013.01); *A61N 5/1049* (2013.01); *A61N 5/1071* (2013.01); *A61N 2005/1052* (2013.01); *A61N 2005/1055* (2013.01); *A61N 2005/1058* (2013.01); *A61N 2005/1061* (2013.01); *A61N 2005/1076* (2013.01)

(58) Field of Classification Search
CPC ......... A61B 6/583; A61B 6/584; A61B 8/587; A61B 2017/00707; A61N 5/1075; A61N 5/1049; A61N 5/1071; A61N 2005/1052; A61N 2005/1055; A61N 2005/1058; A61N 2005/1061; A61N 2005/1076
See application file for complete search history.

(56) References Cited

U.S. PATENT DOCUMENTS

| | | | |
|---|---|---|---|
| 6,238,343 B1 | 5/2001 | Madsen et al. | |
| 6,362,471 B1 | 3/2002 | Spitz et al. | |
| 6,493,574 B1 | 12/2002 | Ehnholm et al. | |
| 7,056,019 B1 | 6/2006 | Hanson et al. | |
| 7,594,753 B2 | 9/2009 | Main et al. | |
| 7,728,285 B2 | 6/2010 | Suh et al. | |
| 7,844,094 B2 | 11/2010 | Jeung et al. | |
| 8,198,579 B2 | 6/2012 | Jeung | |
| 2003/0086535 A1 | 5/2003 | Teppaz et al. | |
| 2003/0122544 A1 | 7/2003 | Parker et al. | |
| 2004/0245447 A1 | 12/2004 | Karasawa | |
| 2007/0038058 A1* | 2/2007 | West | A61N 5/1049 600/407 |
| 2008/0214936 A1 | 9/2008 | Wieringa et al. | |
| 2008/0240364 A1 | 10/2008 | Main et al. | |

(Continued)

OTHER PUBLICATIONS

CIRS "Tissue Stimulation and Phantom Technology", Sep. 4, 2013.

(Continued)

*Primary Examiner* — Nicole M Ippolito
*Assistant Examiner* — Sean M Luck
(74) *Attorney, Agent, or Firm* — Shapiro, Gabor and Rosenberger, PLLC

(57) ABSTRACT

Dosimetrical end-to-end quality assurance devices, systems, and methods for radiation devices using X-ray imaging, optical surface imaging, and electromagnetic navigational systems to position the quality assurance device either absolute or relative in space.

20 Claims, 24 Drawing Sheets

(56) References Cited

U.S. PATENT DOCUMENTS

| | | |
|---|---|---|
| 2008/0261009 A1 | 10/2008 | Kawabata |
| 2009/0250618 A1 | 10/2009 | Simon |
| 2009/0268953 A1 | 10/2009 | Crucs |
| 2009/0285357 A1* | 11/2009 | Khamene .............. A61B 6/08 378/20 |
| 2010/0167251 A1 | 7/2010 | Boutchko et al. |
| 2010/0239144 A1* | 9/2010 | Fichtinger .............. A61B 5/415 382/131 |
| 2011/0027853 A1 | 2/2011 | Bert et al. |
| 2011/0076659 A1 | 3/2011 | Morris et al. |
| 2011/0076660 A1 | 3/2011 | Morris et al. |
| 2011/0200244 A1 | 8/2011 | Ashton et al. |
| 2012/0095329 A1 | 4/2012 | Kamiya |
| 2012/0155617 A1 | 6/2012 | Dutta et al. |
| 2012/0330083 A1 | 12/2012 | Aitkenhead et al. |

OTHER PUBLICATIONS

End-to-End Radiosurgery tests with Lucy Phantom; Radiation Therapy Department Southeast Missouri Hospital, Cape Girardeau, MO, May-Jun. 2008.

Zhong Su, "Investigations of interference between electromagnetic transponders and wireless MOSFET dosimeters: A phantom study," published Apr. 28, 2011, 2011 American Association of Physicists in Medicine.

* cited by examiner

DOSIMETRIC END-TO-END VERIFICATION DEVICES, SYSTEMS, AND METHODS

FIELD

The present disclosure relates generally to radiation therapy systems, devices, and methods, and more particularly to quality assurance end-to-end verification devices for the testing, calibration, and validation of radiation treatment systems, devices, and methods.

BACKGROUND

In radiosurgery or radiotherapy (collectively referred to as radiation treatment), very intense and precisely collimated doses of radiation are delivered to the target region in the body of a patient in order to treat or destroy lesions. Typically, the target region is comprised of a volume of tumorous tissue. Radiation treatment requires an accurate spatial localization of the targeted lesions. Stereotactic radiosurgery (SRS) is a specific type of image-based treatment, which delivers a high dose of radiation during a single session. Because a single radiosurgery dose is more damaging than multiple fractionated doses, the target area must be precisely located.

In general, radiation treatments consist of several phases. First, a precise three-dimensional (3D) map of the anatomical structures in the area of interest (head, body, etc.) is constructed using any one of (or combinations thereof) a computed tomography (CT), cone-beam computed tomography (CBCT), magnetic resonance imaging (MRI), positron emission tomography (PET), 3D rotational angiography (3DRA), ultrasound techniques, single photon emission tomography (SPECT), or biplanar digital subtraction angiography (DSA). This determines the exact coordinates of the target within the anatomical structure, namely, locates the tumor or abnormality within the body and defines its exact shape and size. Second, a motion path for the radiation beam is computed to deliver a dose distribution that the surgeon and/or radiation oncologist finds acceptable, taking into account a variety of medical constraints. During this phase, a team of specialists develop a treatment plan using special computer software to optimally irradiate the tumor and minimize dose to the surrounding normal tissue by designing beams of radiation to converge on the target area from different angles and planes. Third, the radiation treatment plan is executed. During this phase, the radiation dose is delivered to the patient according to the prescribed treatment plan. The imaging modalities in each of these steps are configured to operate within prescribed modes of operation for each type of scan performed.

Generally, quality assurance (QA) and verification protocols are instituted for each stage of the radiation treatment process. The performance of the respective radiation treatment devices, their generated images, and the transfer of those images across digital networks are calibrated and tested by phantom assemblies and devices which, when imaged by the respective imaging modality, generate images that are representative, familiar, and logical to the structure and configuration of the phantom. Systematic testing and measurement of the images should produce measurement values that fall within the range of expected and legally acceptable values which indicate that the imaging device operates within normal or acceptable levels of performance.

Existing verification phantoms include CT phantoms, slab geometry phantoms, and anthromorphic phantoms. CT phantoms are used for checking the CT number relative electron density (RED) conversion, the radiation beam geometry assessments, the digitally reconstructed radiograph (DRR) generation, and multiplanar reconstruction. Slab geometry phantoms are used for film dosimetry and corrections for inhomogeneous geometries. Anthromorphic phantoms are used for dosimetric measurements of typical or special treatment techniques. Each of these phantoms is designed to fulfill a particular verification function at a particular stage of the treatment process.

Currently there is no single universal verification phantom available that can provide end-to-end verification, and which can be simultaneously used with a range of imaging modalities to facilitate image based positioning and monitoring, as well as dosimetric analysis of the delivered dose distribution.

SUMMARY

Embodiments of the present invention provide a universal phantom assembly that can be used to simulate the entire treatment procedure: scanning, targeting, planning, and radiation dose delivery.

Embodiments of the present invention provide a single universal verification phantom that can provide end-to-end verification, and which can be simultaneously used with a range of imaging modalities to facilitate image based positioning and monitoring, as well as dosimetric analysis of the delivered dose distribution.

Embodiments of the present invention provide a phantom assembly that can be used to simulate every stage of a radiation treatment process that a patient would be exposed to, including CT scan, MRI scan, SPECT/PET, biplanar and rotational angiography, isocenter determination, dose planning and calculation, positioning of the phantom (patient) at the treatment device using various kinds of positioning and monitoring systems (kV, MV, computed tomography (CT), cone-beam computed tomography (CBCT), digital tomosynthesis (DTS), magnetic resonance imaging (MRI), optical surface monitoring system, Calypso), irradiation using the determined treatment plan (volumetric modulated arc therapy (VMAT), intensity-modulated radiation therapy (IMRT), conformal arc, cones, high-definition multileaf collimator (HDMLC), multileaf collimator (MLC), three-dimensional conformal radiation therapy (3DCRT) and any combinations), and analysis of the measured dose distribution in order to compare the measured dose distribution with the calculated one in terms of dose volume/area parameters, or in terms of dose localization accuracy to determine the dosimetric isocenter.

Embodiments of the present invention provide a universal verification phantom assembly that allows testing and validating the measurement accuracy of two-dimensional (2D) and three-dimensional (3D) image measurement devices and tools installed on medical imaging devices which are involved in every stage of the radiation treatment process, as well as verification of the measurement accuracy of digital image viewing stations that include diagnostic, clinical review, internet browser and teleradiology network of transferred medical diagnostic image systems.

Embodiments of the present invention provide a three-dimensional phantom assembly that can be used to independently verify the phantom or isocenter position by the use of various positioning systems available on the treatment device, and is able to facilitate image based positioning of the phantom using (kV, MV, computed tomography (CT), cone-beam computed tomography (CBCT), digital tomosynthesis (DTS), magnetic resonance imaging (MRI), optical surface monitoring system, Calypso monitoring).

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features.

DETAILED DESCRIPTION

Figure 1:
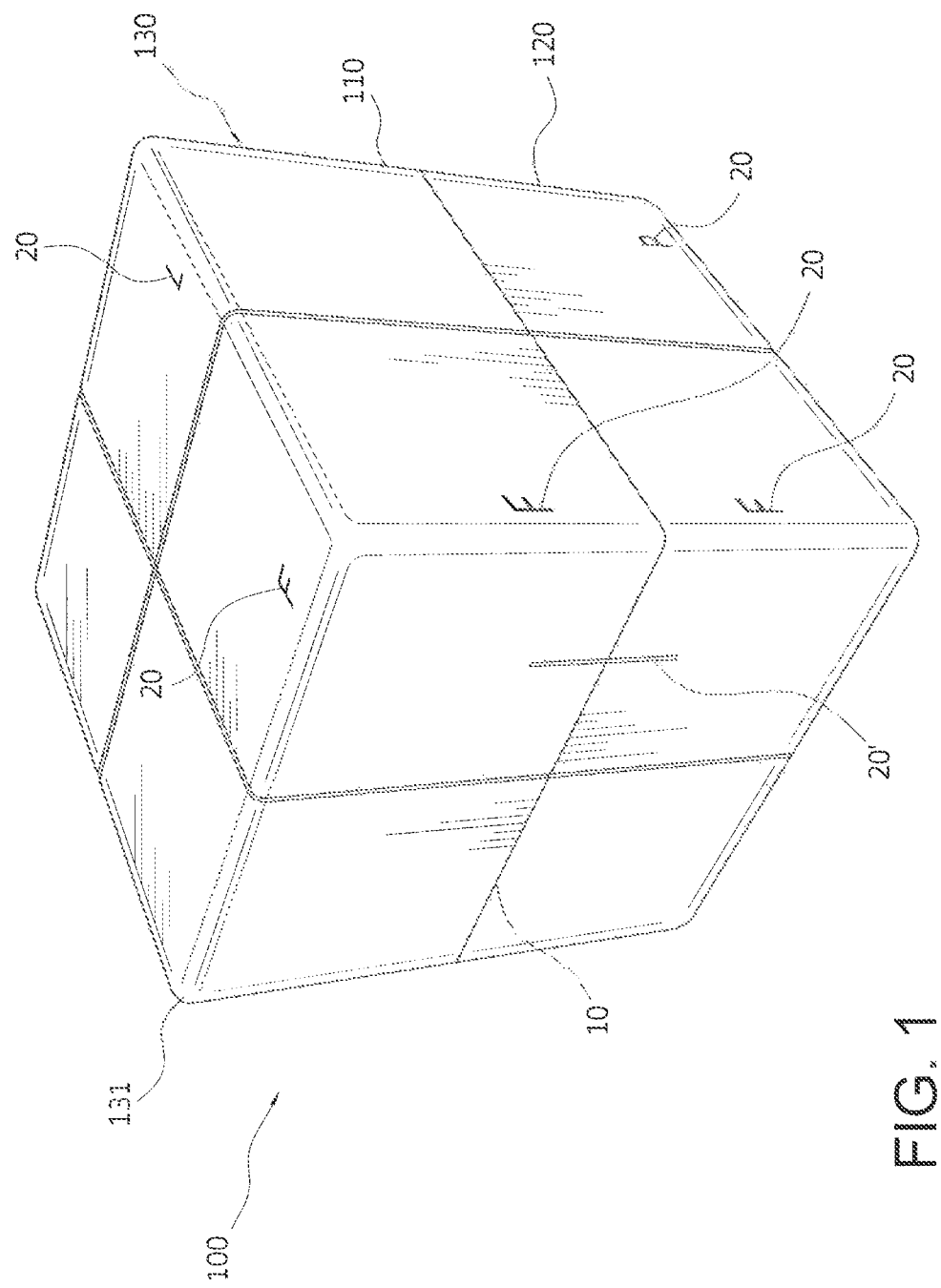
FIG. 1 is a perspective view of a verification phantom in a closed position according to various embodiments of the disclosed subject matter.

Patients undergoing radiation therapy are typically placed on a treatment platform of a radiation treatment gantry. The gantry has a radiation source that is used to generate a radiation beam that irradiates a region of interest in the patient, such as a diseased tissue including a tumor and cancerous growth site. When delivering the radiation, a plurality of radiation beams may be directed to the target area of interest from several positions outside the body. The gantry can be rotated to provide the radiation beams from different positions. The point at which beam trajectories converge or intersect is generally referred to as the isocenter. The isocenter typically receives the largest radiation dose because of the cumulative radiation received from multiple radiation beams. Prior to exposing the patient to the radiation beams, the patient is positioned in the treatment device so that the location of the treatment plan isocenter corresponds with the isocenter of the machine. An integral part of the radiation treatment process is the coincidence of the treatment plan isocenter with the isocenter of the machine. The isocenter coincidence is, however, affected by many factors, one of which is the lack of knowledge regarding the precise location of the machine isocenter. In existing systems, the isocenter of a radiation system is identified by a set of fan-beam room lasers, each of which defines an orthogonal plane. These planes intersect the isocenter to identify that position. Over time, the laser may shift from their original location, which results in a shift of the intersection point. Thus, the intersection point of the laser beams may deviate from the true isocenter location. If the lasers are not realigned to precisely determine the machine isocenter, the coincidence of the treatment plan isocenter with the isocenter of the machine will be affected. The isocenter coincidence is also affected in clinical practice by the radiation treatment workflow, including imaging, target alignment that is often software based, and treatment couch motion.

An object of the invention is therefore to provide an end-to-end phantom assembly that can be used to verify the isocenter alignment device; that mimics clinical radiation treatment workflow and verifies final target alignment based on imaging with the radiation treatment isocenter; and that can aid the assessment of the entire clinical radiation treatment process, including computed tomography (CT) performance, such as, but not limited to, verification of geometric accuracy of the CT data set, placement of the isocenter in the planning systems, transfer of coordinates from CT to linear accelerator through the planning system, couch motion, imaging alignment, beam collimation, and coincidence of the imaging isocenter with the radiation isocenter.

Another object of the invention is to provide a phantom assembly that can be used to execute quality assurance processes to ensure that the radiation treatment delivery system is properly aligned and configured as specified to accurately deliver a prescribed dose of radiation to the patient. The phantom assembly can validate that the imaging system, the positioning system, the treatment couch, and the radiation source are all calibrated and aligned with each other. Moreover, it can verify coincidence of the imaging isocenter with the radiation isocenter, verify software-based alignments, and verify correct couch and gantry shifts, pitch and roll angles, as well as rotations, based on exact knowledge of the geometry of the phantom.

Another object of the invention is to provide a phantom assembly which allows simulation of all of the functions of the radiation therapy system which use X-ray imaging, optical surface imaging, and Calypso imaging to position the phantom either absolute or relative in space. The phantom can be used to independently verify the phantom or isocenter position by the use of various positioning systems available on the treatment device and is able to quantitatively determine a shift between the different isocenter/imaging centers used.

Another object of the invention is to provide a phantom assembly which facilitates image based positioning of the phantom using kilovoltage (kV), megavoltage (MV), optical surface, and Calypso monitoring.

Another object of the invention is to provide a phantom assembly which facilitates dosimetric analysis of the delivered dose distribution in order to determine the absolute or relative dose distribution or point dose values.

FIGS. 1-4 illustrate a universal three-dimensional phantom assembly 100 that can fulfill the above described objects. In general, the phantom assembly 100 is a precisely machined phantom (mechanical accuracy <1/10 mm) including an outer housing assembly 130 which can include a plurality of embedded fiducials, markers, and transponders to facilitate image based positioning and monitoring, as well as an interchangeable inner dosimetric insert 200, positioned within the outer housing assembly 130, which can include one or more dosimetric measuring devices, to facilitate dosimetric analysis of the delivered dose distribution. A variety of interchangeable dosimetric inner inserts 200 can be used within the outer housing 130 to form the phantom 100.

Figure 2:
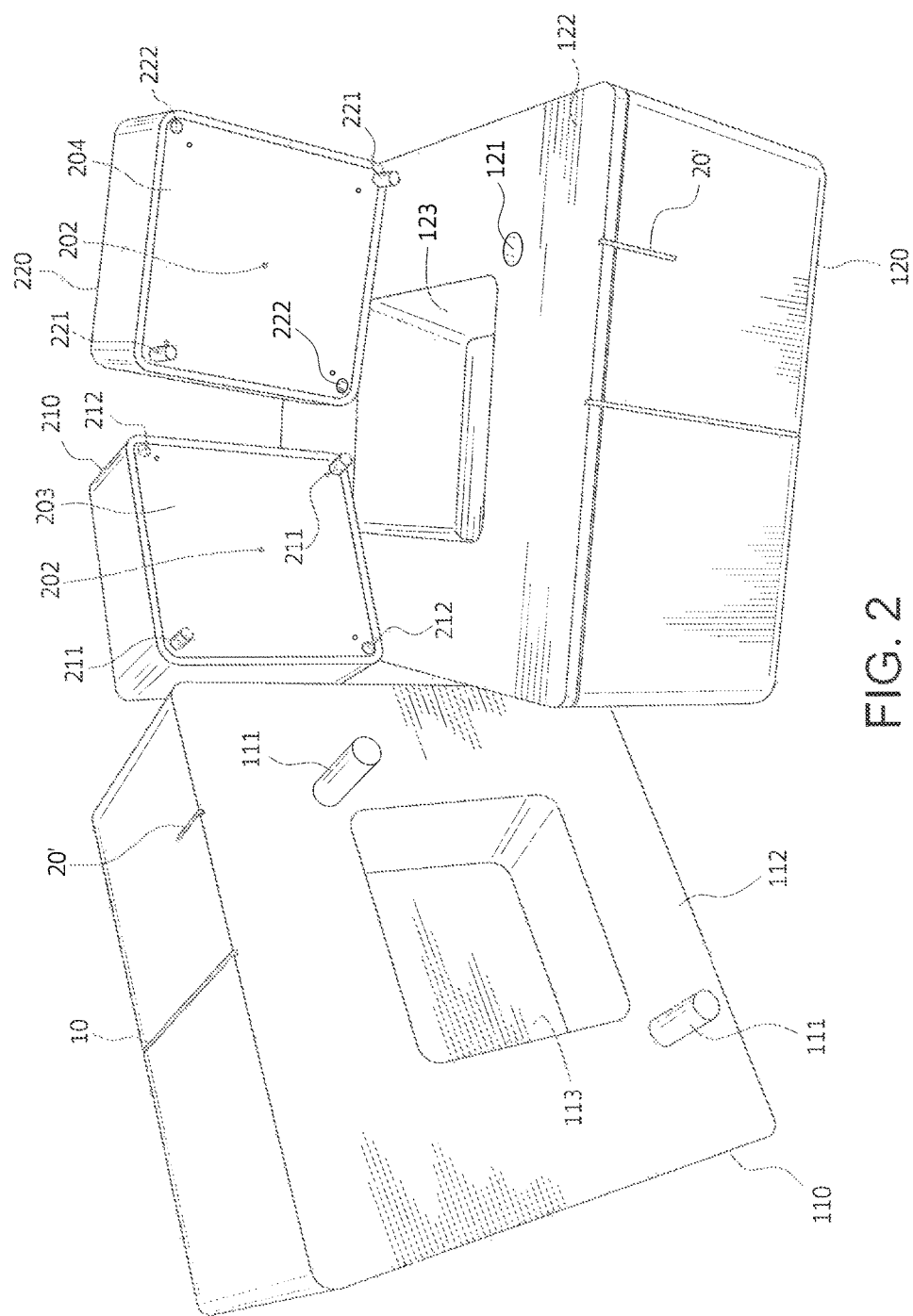
FIGS. 2-4 are perspective views of a verification phantom in an open position according to one or more embodiments of the disclosed subject matter.

In an illustrative embodiment, the phantom 100 is a cubic phantom having a cube shaped outer housing 130 with sides that are approximately 150 mm long forming a 15×15×15 $cm^3$ outer cube as shown in FIG. 1. The outer housing 130 can be formed by the assembly of two rectangular housing pieces 110 and 120, as shown in FIG. 2. When assembled together, the two rectangular housing pieces 110 and 120 constitute the outer cube 130. The phantom 100 can include visible cross hair alignment marks 10 on all six (6) outer faces of the outer housing 130, as well as other fiducial markings, such as letter markings 20 (letters F, L, P, for example), as shown in FIGS. 1-10, and discussed in detail below.

Figure 3:
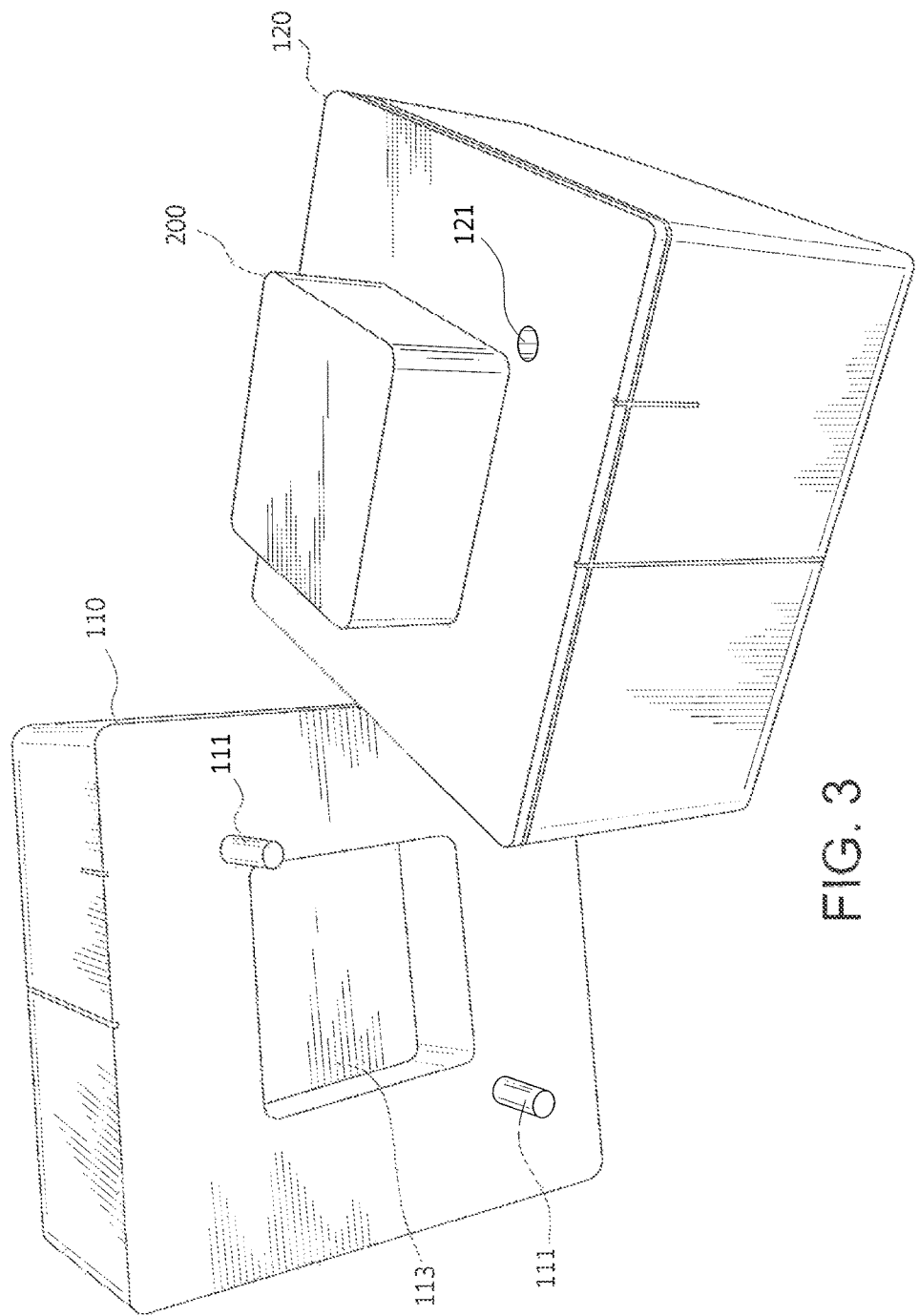
Figure 4:
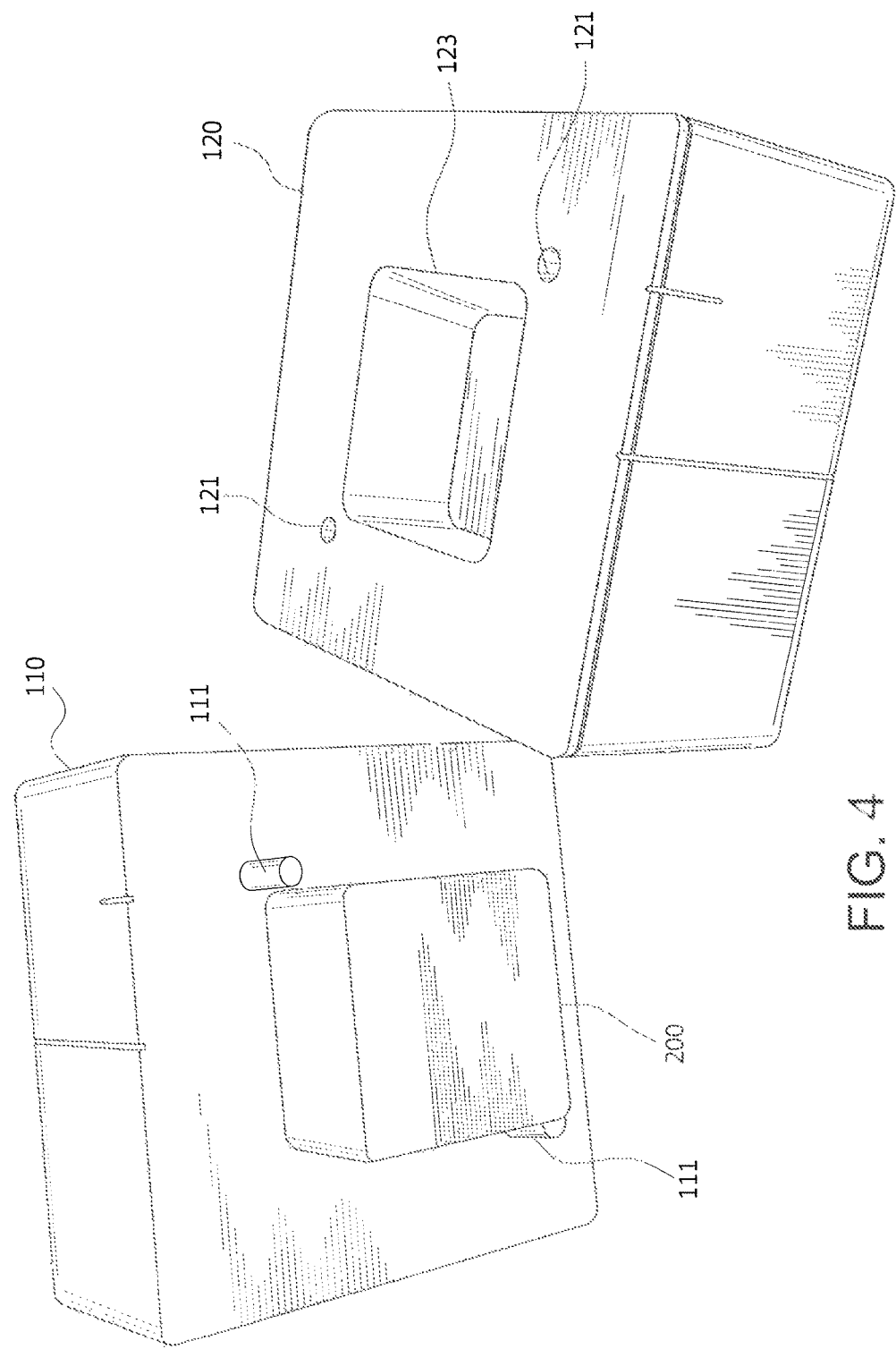

To form the outer housing 130, the two housing pieces 110 and 120 are assembled together using connectors, such as, pegs, pins, screws, bolts, rivets, nails, or any other connecting/fastening/locking mechanisms. In an exemplary embodiment, one of the housing pieces 110 includes two pins 111 positioned on a surface 112 of the first housing piece 110 so as to face corresponding holes/cavities 121 located on an opposing surface 122 of the second housing piece 120, as shown in FIGS. 2-4. To assemble the outer housing 130, the pins 111 of the first housing piece 110 slide into the corresponding holes 121 of the second housing piece 120. The two housing pieces 110 and 120 are maintained in an assembled position by the friction between the pins 111 and the surface of the holes/cavities 121. The pins 111 can be made of a plastic material, such as, but not limited to, polyvinyl chloride (PVC), and each can have a diameter of about 5 mm. The pins 111 can also be made of a material that can simulate bone density. The corresponding holes 121 each have a diameter of approximately 5 mm so as to allow insertion of the pins 111 therewithin and assembly and connection of the two housing pieces 110 and 120 to each other through friction.

The outer housing 130 including the two housing pieces 110 and 120 can be formed of a variety of materials that are transparent, or at least translucent, to imaging beams (e.g., X-rays) and are penetrable by the imaging beams. The outer housing 130 can be made of plastic, such as, but not limited to, polyurethane. The outer housing 130 can also be made of a material that mimics a tissue or organ, such as a material having a density of 0.45 $g/cm^3$ to mimic/simulate the lung, for example. All edges 131 of the outer housing 130 can also be rounded to avoid imaging artifacts, such as CT artifacts. In one embodiment the edges are rounded so as to follow an arcuate path having a 5 degree arc.

Although the illustrated embodiment includes a cubic outer housing 130 having particular dimensions and material, it should be appreciated that outer housing 130 may assume other shapes, materials, or dimensions. The phantom 100 is also compatible with various stereotactic fixation devices, such as, but not limited to stereotactic frames and mask systems, and other fixation devices that allow the phantom to be secured to different radiation treatment devices and systems to perform end-to-end calibration and verification tests.

FIG. 2 illustrates the cubic phantom assembly 100 in an open position showing outer housing 130 in an open form, and the rectangular housing pieces 110 and 120 separated from each other. Each of the housing pieces 110, 120 includes a corresponding recess 113, 123 at substantially the center location of each of the rectangular housing pieces 110, 120. When assembled together, the housing pieces 110 and 120 form a composite recess within the center portion of the phantom assembly 100. The size of the composite recess is such that it can accommodate an inner dosimetric insert 200, having sides approximately 70 mm long, forming a 7×7×7 $cm^3$ cubic dosimetric insert 200, as shown in FIGS. 3 and 4. The inner insert 200 is intended to represent a target region including a volume of interest that represents a tumorous or other lesion within a patient at which the radiation treatment delivery treatment system is directed to treat with radiation. The purpose of this inner insert 200 is to facilitate dosimetric analysis of the delivered dose distribution. The inner insert 200 may be formed of a variety of materials, such as, but not limited to, plastics, including polyurethane. All edges of the inner insert 200 can also be rounded to avoid imaging artifacts. In one embodiment, the edges are rounded so as to follow an arcuate path having a 5 degree arc. In embodiments, the inner insert 200 can be made of a soft tissue simulating/mimicking material. In one embodiment, the density of the inner insert material is 1.05 $g/cm^3$ to simulate soft tissue having the approximate density of water, which is 1.0 $g/cm^3$. Although the illustrated embodiment includes a cubic inner insert 200 having particular dimensions and material, it should be appreciated that the inner insert 200 may assume other shapes, materials, or dimensions.

Figure 7:
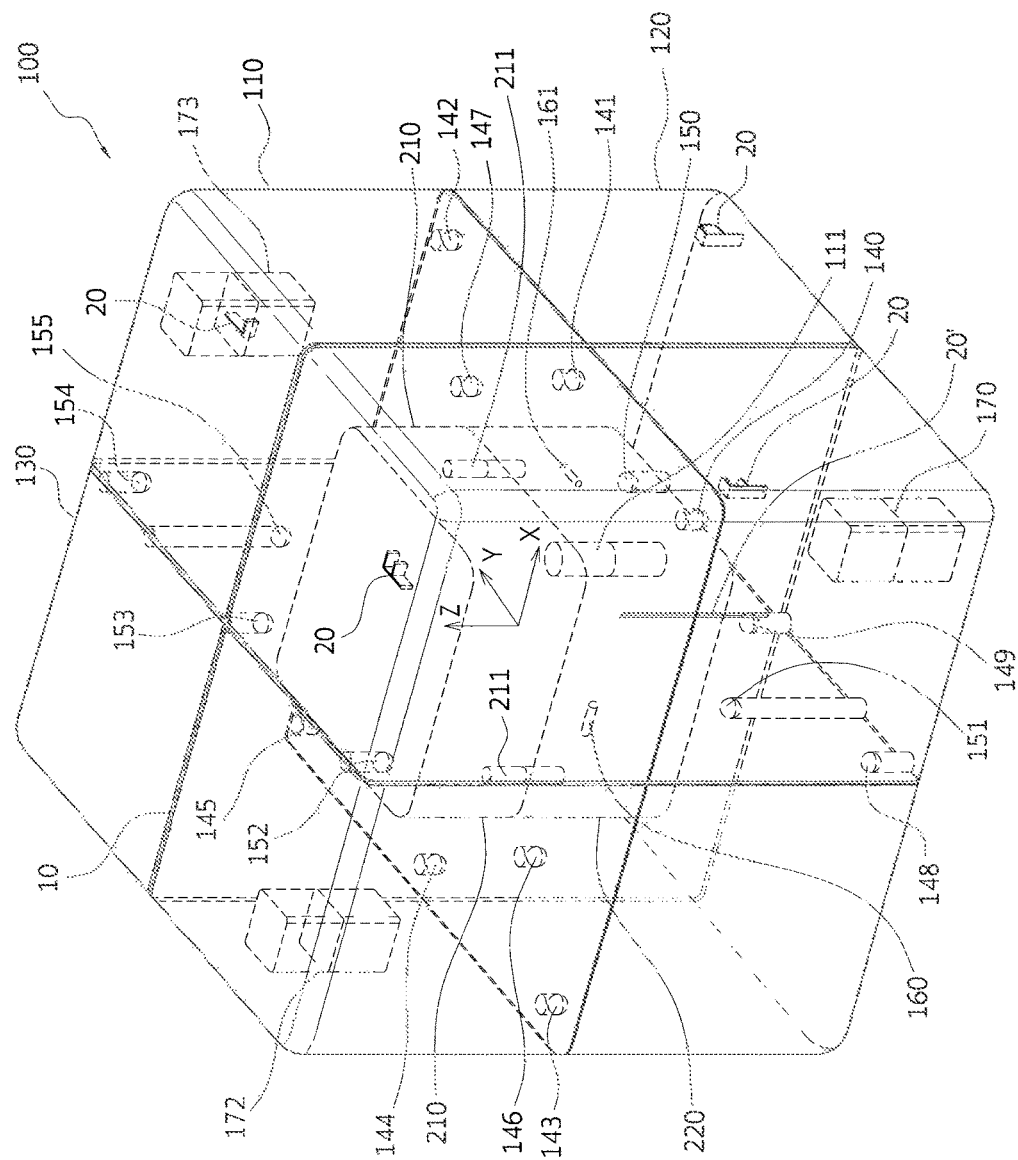
FIGS. 7 and 8 are different 3D views of verification phantoms with elements inside phantoms according to one or more embodiments of the disclosed subject matter.

The inner insert 200 is positioned within the outer housing 130 so that the center 202 of the inner insert 200 corresponds with the center of the outer housing assembly 130 and the center of the phantom 100, as shown in FIG. 7. The inner insert 200 can be positioned at the center of the outer housing 130 so that the center of the phantom 100 is located at the center 202 of the inner insert 200 at the X=0, Y=0, Z=0 position in an X, Y, Z coordinate system.

Figure 5:
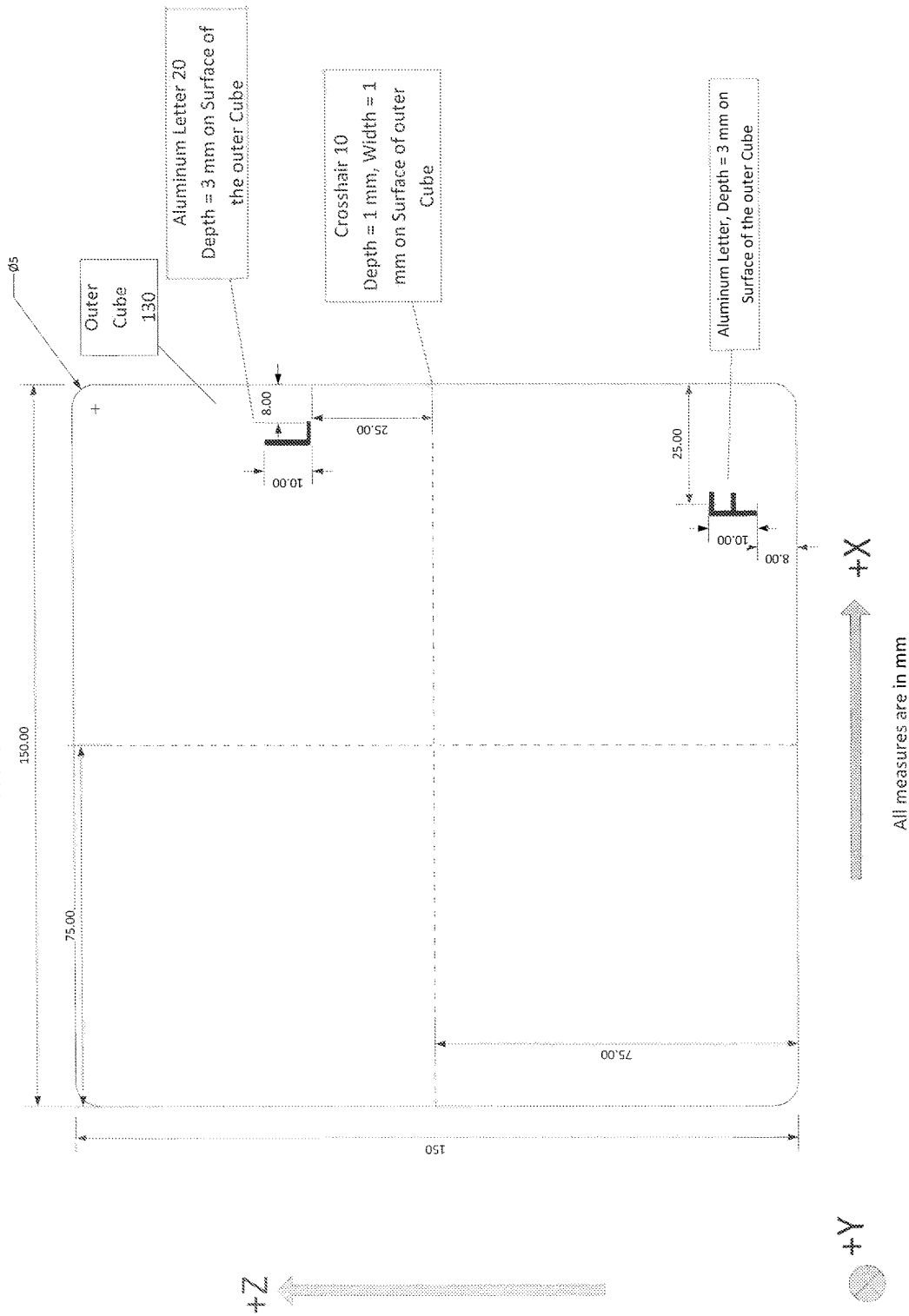
FIG. 5 is a top plan view of a verification phantom according to one or more embodiments of the disclosed subject matter.
Figure 6:
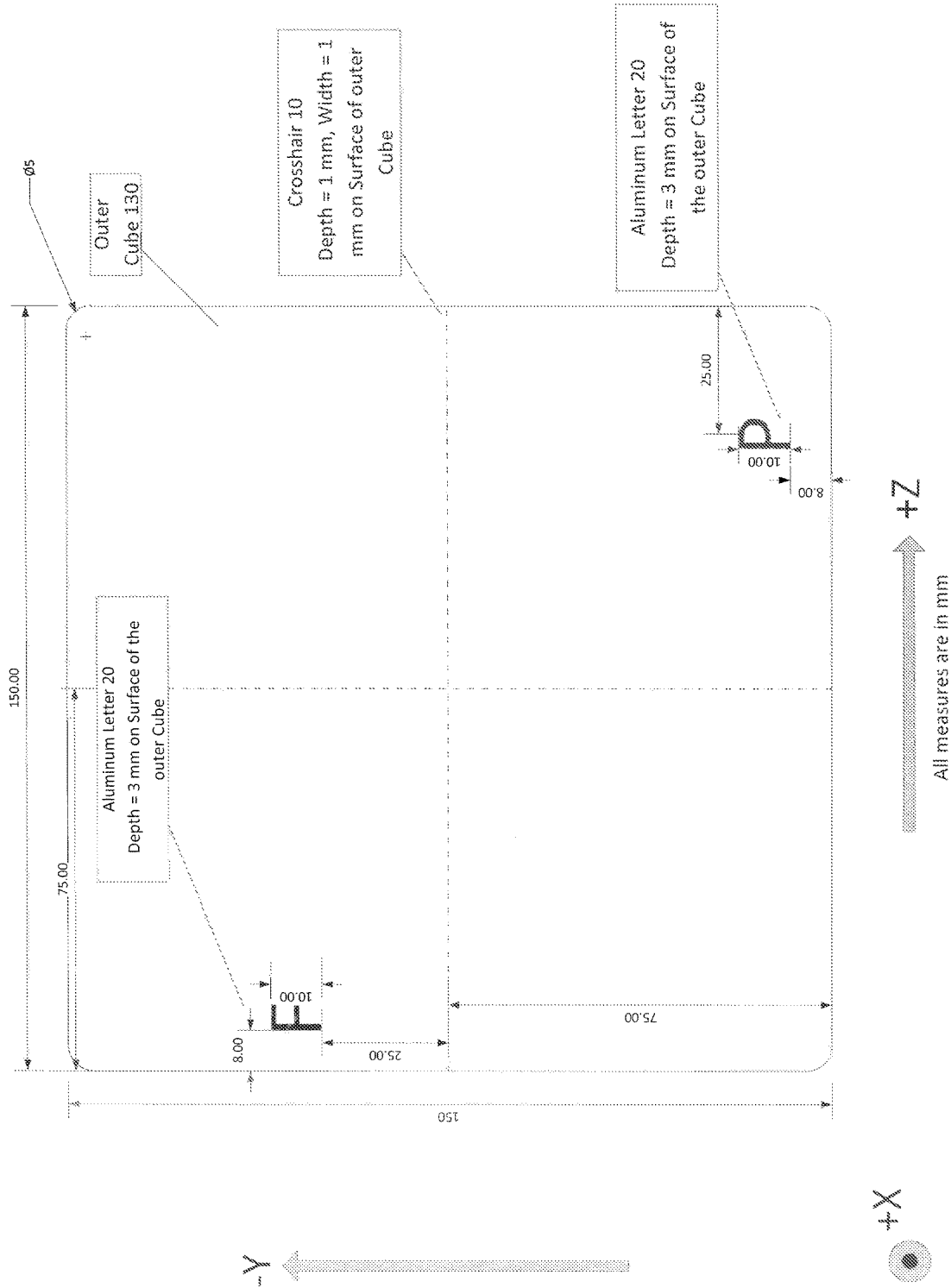
FIG. 6 is a side plan view of a verification phantom according to one or more embodiments of the disclosed subject matter.

The phantom 100 can also include visible cross-hair alignment markings 10 on all six (6) outer faces of the outer housing 130, as well as other fiducial markings, such as letter markings 20 (letters F, L, P, for example), and line markings 20' as shown in FIGS. 1, 5, and 6. FIG. 5 illustrates a top view of the phantom 100 including the cross-hair alignment markings 10, line markings 20', and the letter markings 20 etched into the outer housing 130 of the phantom 100. The cross-alignment markings 10 can have a depth of about 1 mm and a width of about 1 mm, and can be precisely positioned on the outer surface of the phantom 100 so as to intersect in the middle of each of its respective six outer surfaces. FIG. 5 also illustrates letter markings F and L etched into an upper surface of the housing piece 110. The depths of the etchings are about 3 mm. Each of the letters is approximately 10 mm long and is precisely positioned relative to the center of the phantom 100. The letter F is positioned such that the middle point along the length of the letter F is positioned at (X=50 mm, Y=-75 mm, Z=-62 mm) from the center location (X=0, Y=0, Z=0) of the phantom 100. The letter L is positioned such that the middle point along the length of the letter L is positioned at (X=62 mm, Y=-75 mm, Z=30 mm) from the center location (X=0, Y=0, Z=0) of the phantom 100.

FIG. 6 illustrates a side view of the phantom 130, with the letters P and F etched into a side surface of the bottom housing piece 120 of the outer housing 130. Each of the letters is approximately 10 mm long and is precisely positioned relative to the center of the phantom 100. The letter P is positioned such that the middle point along the length of the letter P is positioned at (X=75 mm, Y=62 mm, Z=50 mm) from the center location (X=0, Y=0, Z=0) of the phantom 100. The letter F is positioned such that the middle point along the length of the letter F is positioned at (X=75 mm, Y=-30 mm, Z=-65 mm) from the center location (X=0, Y=0, Z=0) of the phantom 100. One or more additional letters can be positioned on the surface of the outer housing 130.

The letter markings can be made of a material such as aluminum having a density of about 2.70 g/cm$^3$, for example. Any other metal besides aluminum, such as copper, for example, can be used for the letter markings. The number and material for the lettering, however, is only illustrative and any fewer or more letter markings can be used.

Other geometric configurations could be substituted for the letter markings. The line-marking 20', cross-hair markings 10, the letter markings 20, and/or the geometric configurations can be used for precision setup of the housing 130, the inner dosimetric insert 200, as well as the phantom 100 in the treatment and/or calibration devices. Each of these letter markings and/or geometric configurations can also be used to verify the capacity of the software used for automatic contouring operations for organs of different densities during target volume reconstruction.

The cubic outer housing 130 can also be embedded and/or impregnated with tracking fiducials such as markers and transponders. Markers in the phantom 100 can be used to determine geometric parameters for the radiation treatment system. Geometric parameters refer to variables associated with an operation of the system, such as, but not limited to, a position component of the system, distance between two components of the system, a source-to-imager distance (SID), a source-to-axis distance (SAD), an axis of rotation, a center of rotation, a piercing point, an isocenter, or the like. The various geometric parameters can be used in different applications. For example, SID and SAD and piercing point information can be used as parameters for cone-beam CT reconstructions, the rotation center can be used to calibrate alignment lasers associated with the system, and/or to corroborate alignment of dual-plane imaging systems, and/or to verify shifts and rotations of the gantry and/or treatment couch.

The transponders, such as electromagnetic transponders, in the phantom 100 can be used to communicate with an electromagnetic navigational system, such as, but not limited to, a Calypso localization systems, using radiofrequency waves. A Calypso system is an electromagnetic, transponder-based, target localization and monitoring system, including an electromagnetic array which contains an energy source that can excite the transponders and receivers that detect each transponder's frequency to determine its location coordinates. Each of the transponders transmits a unique non-ionizing radiofrequency signal to the array, generating position and motion information about the target in which it is imbedded. The transponder's location is subsequently correlated to the treatment or machine isocenter through optical reflectors on the detector. A user interface can display the positional information both inside and outside of the treatment room. The system can also be multiplexed so that multiple transponders tuned at different frequencies can be discretely detected. The electromagnetic transponders and the Calypso system can also provide target localization and monitoring during radiation treatment delivery. During radiation treatment, the transponders and the Calypso system can provide the clinician continuous, real-time monitoring of the target and can alert the clinician when the target is outside of acceptable boundaries due to organ motion, thereby enabling corrections during the treatment delivery.

Figure 8:
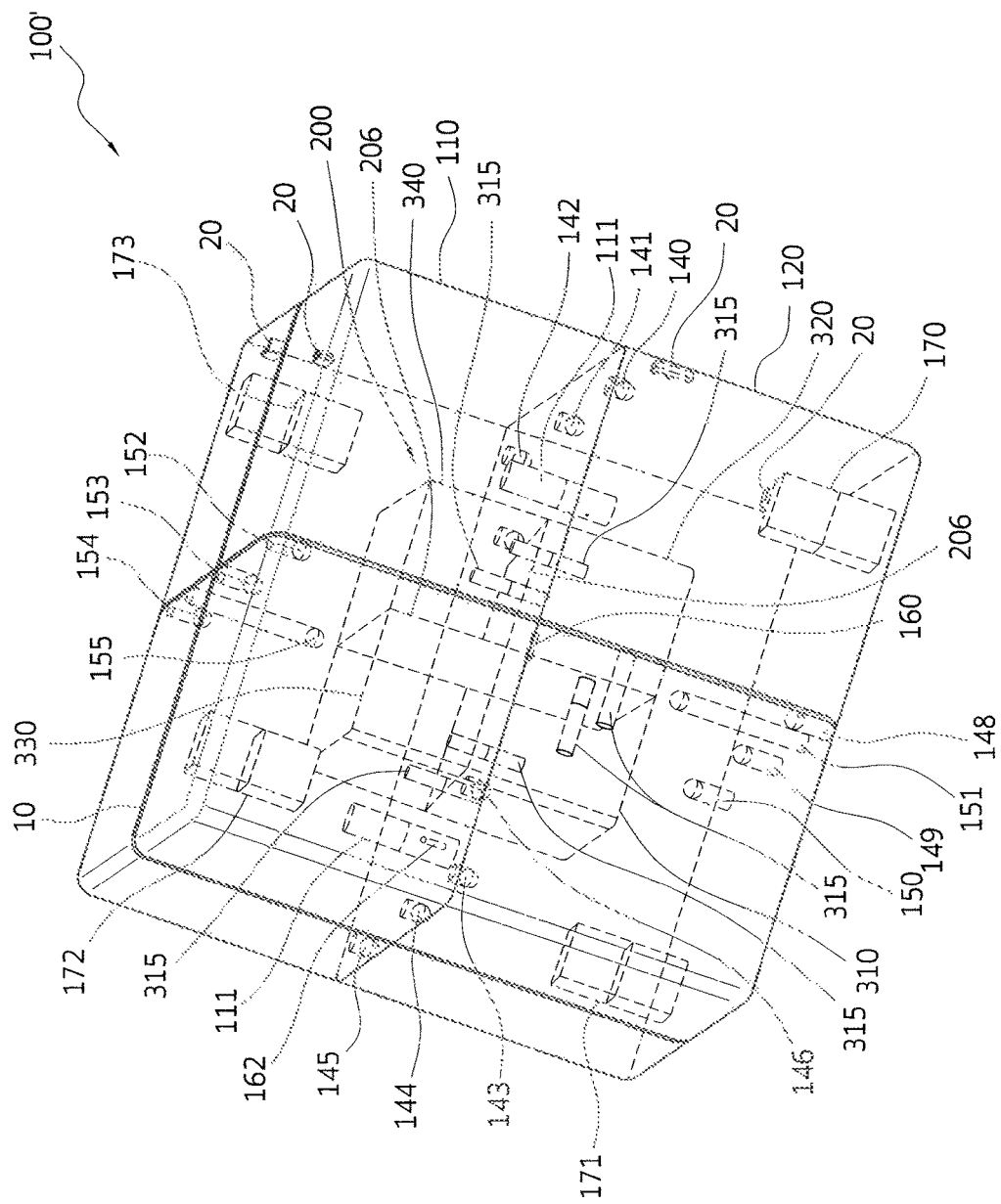

In an illustrative embodiment, sixteen markers 140-156 are regularly distributed throughout the cubic outer housing 130, as shown in FIGS. 7 and 8. Each of the markers can be a radio-opaque marker, such as a ceramic BB (sphere) having a 5 mm diameter cross-section. In embodiments, the ceramic BB sphere markers 140-156 can be made of Al$_2$O$_3$. The BB sphere markers 140-155 can be distributed within the housing 130 so that twelve (12) of the markers are embedded within one of the housing pieces 110, 120, and the remaining four (4) of the BB markers are embedded within the other housing piece. One way to embed the markers into the outer housing 130 is by machining inserts with positioning grooves precisely matching the dimensions of the markers. However, other embedding/impregnating methods may be used. Six of the BB markers 140-145 are embedded in the upper surface 122 of the housing piece 120 so as to be positioned along two opposing upper edges (sides) of housing piece 120, with three markers 140-142 located along one of the edges and three markers 143-145 along the opposing edge, each approximately 10 mm from the edges of the housing piece 120. The center of each of the markers 140-145 is positioned approximately 65 mm from the center of the phantom 100 along the X axis, with marker 140 located at (X=65 mm, Y=5 mm, Z=-65 mm), marker 141 located at (X=65 mm, Y=5 mm, Z=0 mm), marker 142 located at (X=65 mm, Y=5 mm, Z=65 mm), marker 143 located at (X=-65 mm, Y=5 mm, Z=65 mm), marker 144 located at (X=−65 mm, Y=5 mm, Z=0 mm) and marker 145 located at (X=−65 mm, Y=5 mm, Z=65 mm).

Two BB sphere markers 146-147 are embedded in the upper surface 122 of the housing piece 120 approximately 40 mm from the center of the phantom 100 along the X axis and approximately 40 mm from the center of the phantom 100 along the Y axis, at locations which are adjacent to diagonally opposing corners of the recess 123 of the housing piece 120, with the center of marker 146 located at (X=−40 mm, Y=5 mm, Z=−40 mm) and the center of marker 147 located at (X=40 mm, Y=5 mm, Z=40 mm). Three BB sphere markers 148-150 can be embedded within a middle portion of the bottom surface of the housing piece 120, approximately 10 mm from the bottom of the housing piece 120, with the center of marker 148 located at (X=0 mm, Y=+65 mm, Z=−65 mm), the center of marker 149 located at (X=0 mm, Y=65 mm, Z=0 mm), and the center of marker 150 located at (X=0 mm, Y=65 mm, Z=65 mm). The twelfth marker 151 is also embedded in housing piece 120 at (X=0 mm, Y=−40 mm, Z=−40 mm).

The remaining four BB sphere markers 152-155 can be embedded within the housing piece 110, such that three BB sphere markers 152-154 are embedded within a middle portion of the upper surface of the housing piece 120, approximately 10 mm from the upper edge of the housing piece 110, forming a mirror image of the three BB sphere markers 148-150 embedded in the housing piece 120, with the center of marker 152 located at (X=0, Y=−65 mm, Z=−65 mm), the center of marker 153 located at (X=0 mm, Y=−65 mm, Z=0 mm), and the center of marker 154 located at (X=0 mm, Y=−65 mm, Z=65 mm). The sixteenth marker 155 is also embedded in housing piece 120 at (X=0 mm, Y=−40 mm, Z=40 mm) so as to diagonally oppose marker 151.

The illustrated embodiment includes a total of sixteen (16) markers 140-155. However, the phantom 100 can have fewer or more than sixteen markers. Also, in the illustrated embodiment, the markers 140-156 are positioned relative to each other such that they collectively form a regular pattern. However, in other embodiments, the markers 140-155 can be positioned such that the markers collectively form an irregular pattern. Also, instead of embedding the markers 140-156 into the walls of the outer housing 130, the markers 140 can be secured permanently or detachably to interior surfaces of the outer housing 130 using securing mechanism, such as, Velcro, pins, clamps, screws, bolts, clips, or the like. In an alternative embodiment, the markers 140-155 can be other than radio-opaque markers and can have cross-sections that are between 2-5 mm, or any other cross-sections.

The phantom 100 can also include three electromagnetic transponders 160-162 embedded into the outer housing 130 at precise locations as illustrated in FIGS. 7 and 8. One way to embed the transponders into the outer housing 130 is by machining inserts with positioning grooves precisely matching the dimensions of the transponders. However, other methods may also be used to embed the transponders into the outer housing 130 of phantom 100. Each of the electromagnetic transponders can be made of a material including glass housing with a ferrite core and each can be approximately 9 mm long and has a 2 mm cross-section. Each of the transponders can transmit a unique non-ionizing radiofrequency signal.

A first (apex) transponder 160 is positioned approximately 45 mm from the center (X=0, Y=0, Y=0) of the phantom 100, with the center of the transponder located at (X=0 mm, Y=0 mm, Z=−45 mm), a second (left base) transponder 161 is positioned approximately 45 mm from the center of the phantom 100, with the center of the second transponder located at (X=45 mm, Y=0 mm, Z=−5 mm), and a third (right base) transponder 162 is positioned approximately 45 mm from the center of the phantom 100, with the center of the third transponder located at (X=−45 mm, Y=0 mm, Z=5 mm). The first transponder 160 is positioned so that its length extends along the X axis, the second transponder 161 is positioned so that its length extends along the Y axis, and the third responder 162 is positioned so that its length extends along the Z axis.

The illustrated embodiment includes a total of three (3) transponders 160-162, with the first transponder 160 being responsive to a 300 kHz frequency, the second transponder 161 being responsive to a 400 kHz frequency, and the third transponder 162 being responsive to a 500 kHz frequency. The transponders 160-162 can be Beacon electromagnetic transponders that are configured to communicate with a Calypso localization system using radiofrequency waves for target localization and monitoring. The phantom 100, however, can have fewer or more than three transponders, and different frequencies. In the illustrated embodiment, the transponders arc positioned relative to each other such that they collectively form a regular pattern. However, in other embodiments, the transponders can be positioned such that the transponders collectively form an irregular pattern.

Figure 9:
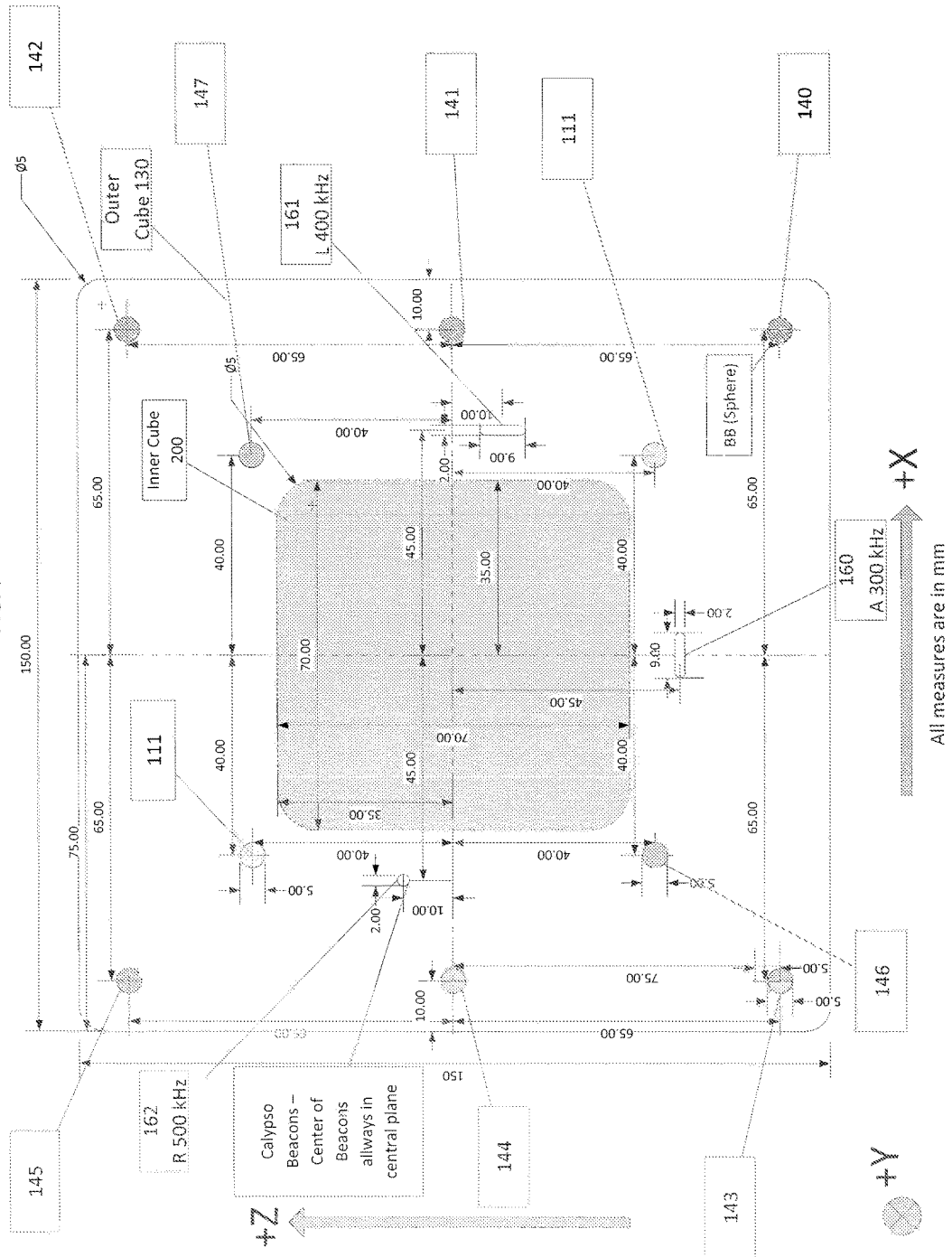
FIG. 9 is a plan view (coronal plane, anterior-posterior view) illustrating positions of elements within of a verification phantom according to one or more embodiments of the disclosed subject matter.
Figure 10:
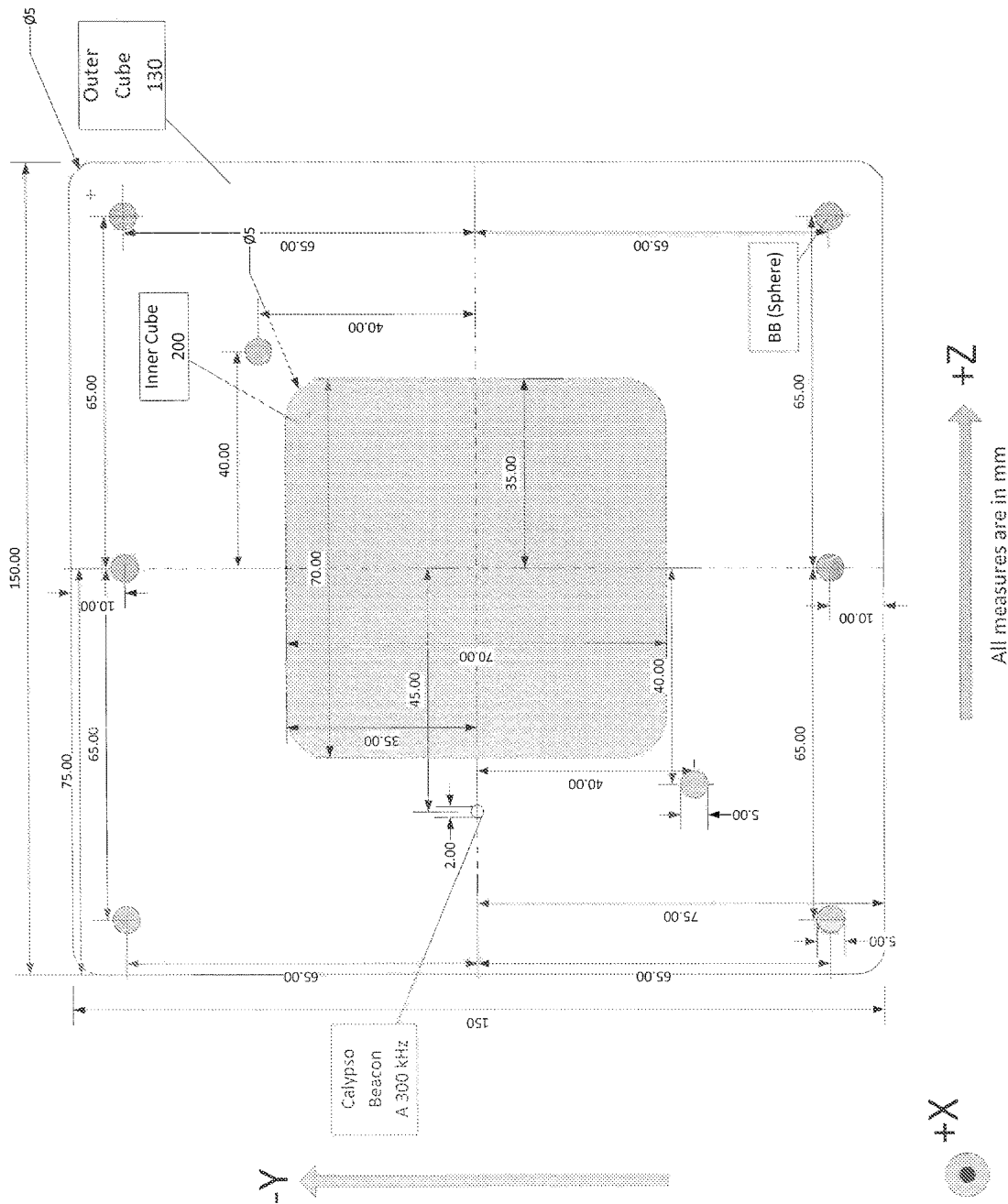
FIG. 10 is a plan view (sagittal plane, left-right view) illustrating positions of elements within a verification phantom according to one or more embodiments of the disclosed subject matter.

The exemplary locations and dimensions of the different elements (markings, transponders, pins, etc.) embedded in the phantom 100 are further illustrated in FIG. 9, which is a plan view of the phantom in a coronal plane (anterior-posterior view, isocenter plane: Y=0), and in FIG. 10, which is a plan view of the phantom 100 in a sagittal plane (left-right view, isocenter plane: X=0).

The phantom 100 can further include one or more density inserts 171-173 embedded within the outer housing 130 at specific locations. These density inserts 171-173 can have specific geometries and different densities and can represent different densities of different organs and media of the human body, which the radiation beam of the radiation treatment device may pass through. Density inserts are helpful to improve the accuracy of the image matching algorithms and to generate a spectrum of different grey values in the images to more closely reflect the one in patients.

Figure 11:
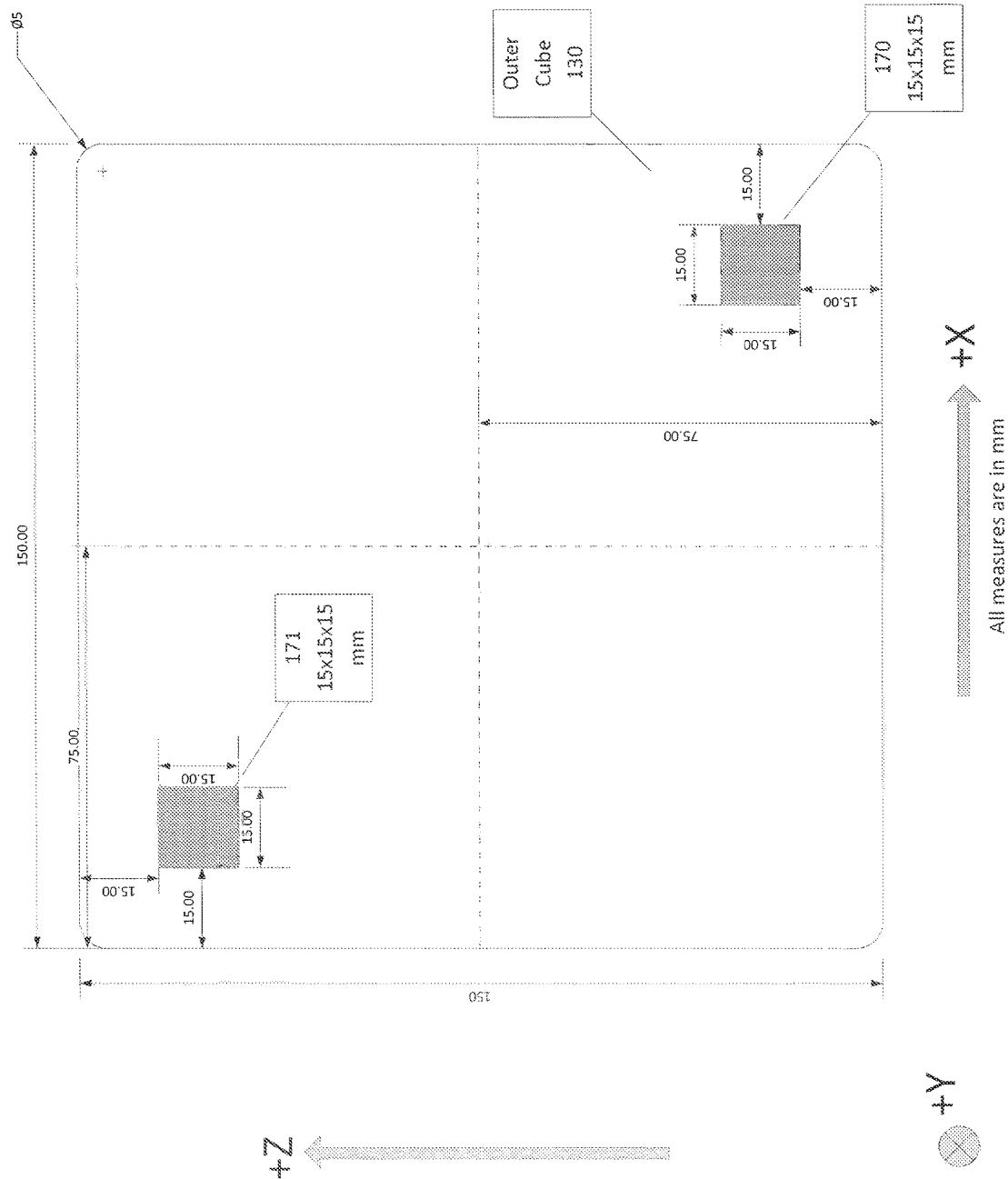
FIGS. 11 and 12 are plan views (coronal plane, anterior-posterior views) illustrating positions of density inserts within a verification phantom according to one or more embodiments of the disclosed subject matter.
Figure 12:
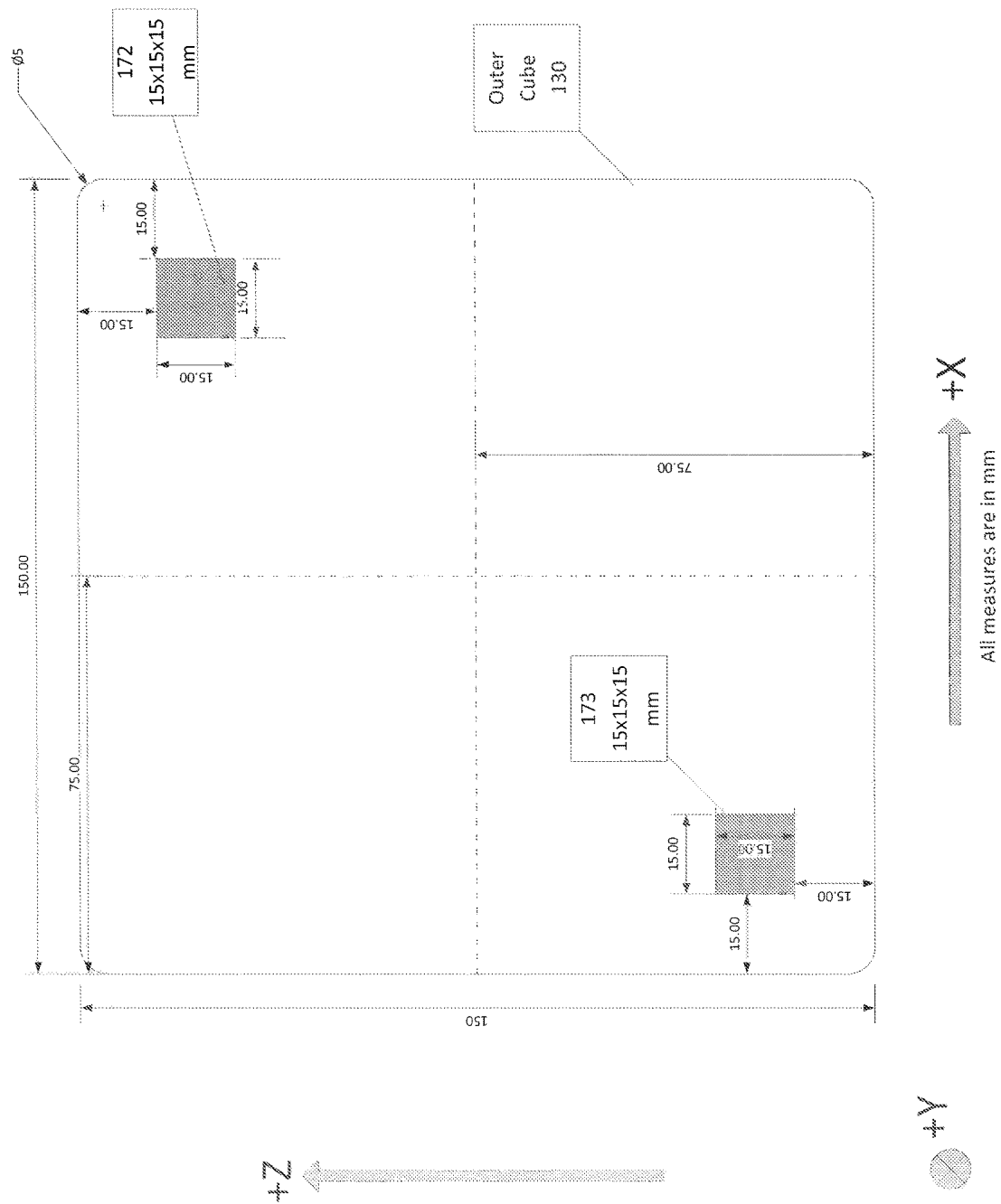

Density inserts 170-173 each can have a cubic shape with sides 15 mm long, for example. Two density inserts 170 and 171 can be embedded in the lower housing piece 120 so as to be positioned at diagonally opposing corners of the housing piece 120, with element 170 having its center located at (X=52.5 mm, Y=+52.5 mm, Z=−52.5 mm) and element 171 having it center located at (X=−52.5 mm, Y=52.5 mm, Z=+52.5 mm) from the center of the phantom 100. The other two density inserts 172-173 can be embedded in the upper housing piece 110 so as to be positioned at diagonally opposing corners of the housing piece 110, with element 172 having its center located at (X=52.5 mm, Y=−52.5 mm, Z=52.5 mm) and element 173 having it center located at (X=−52.5 mm, Y=−52.5 mm, Z=−52.5 mm) from the center of the phantom, as shown in FIGS. 7 and 8. FIG. 11 is a planar view of the phantom with density inserts 170, 172 in a coronal plane (anterior-posterior view), and FIG. 12 is a planar view of density inserts 171, 173 in the coronal plane (anterior-posterior view).

Density inserts 170 and 172 can be formed of materials that mimic bone density and density inserts 171 and 173 can be made of materials that mimic lung density. The bone simulating inserts can be made of PVC and can have a density of 1.42 g/cm³ and the lung simulating inserts can be made of polyurethane and can have a density of 0.25 g/cm³, for example. Any other materials and/or combination of density inserts with different materials, however, can be used. Also, the illustrated embodiment includes a total of four (4) density inserts 170-173. However, the phantom 100 can have fewer or more than four density inserts.

In the illustrated embodiment, the density inserts 170-173 are positioned relative to each other such that they collectively form a regular pattern. However, in other embodiments, the density inserts 170-173 can be positioned such that the inserts collectively form an irregular pattern. Also, instead of embedding the density inserts 170-173 into the walls of the outer housing 130, the inserts 170-173 can be secured permanently or detachably to interior surfaces of the outer housing 130 using securing mechanism, such as, Velcro, pins, clamps, screws, bolts, clips, or the like. In an alternative embodiment, the density inserts 170-173 can be formed of other than the illustrative tissue or organ simulating materials and can have other cross-sections.

In an illustrative embodiment, the dosimetic inner insert 200 includes two separate rectangular insert pieces 210 and 220, which when assembled together form the inner cubic insert 200, as shown in FIGS. 2-4. The inner cubic insert 200 can be positioned inside the composite recess within the outer housing 130 so as to nest within the composite recess when the two housing pieces 110, 120 are assembled together. When the housing 130 is assembled together, the first insert piece 210 rests in the recess 113 of the first housing piece 110 and the second insert piece 220 rests in the recess 123 of the second housing piece 120. The insert pieces 210 and 220 can be formed of a material such as polyurethane having a density of 1.05 g/cm³, for example, which can simulate a soft tissue. However, the insert pieces 210 and 220 can also be made of any other materials having different densities which can represent different densities of different organs and media of the human body through which the radiation beam of the radiation treatment system may pass.

Figure 13:
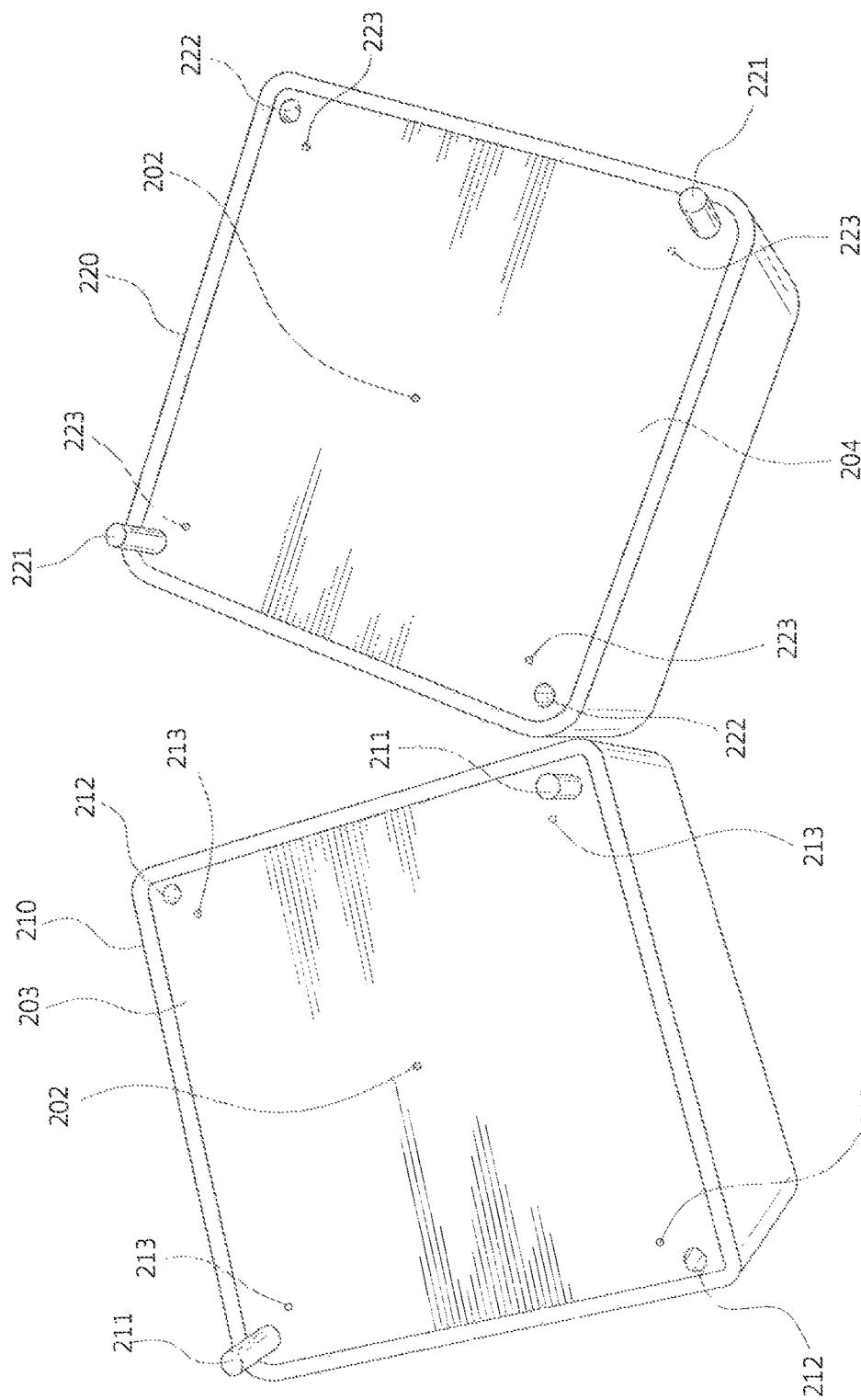
FIG. 13 is a top perspective view of a dosimetric insert in an open position of a verification phantom according to one or more embodiments of the disclosed subject matter.
Figure 14:
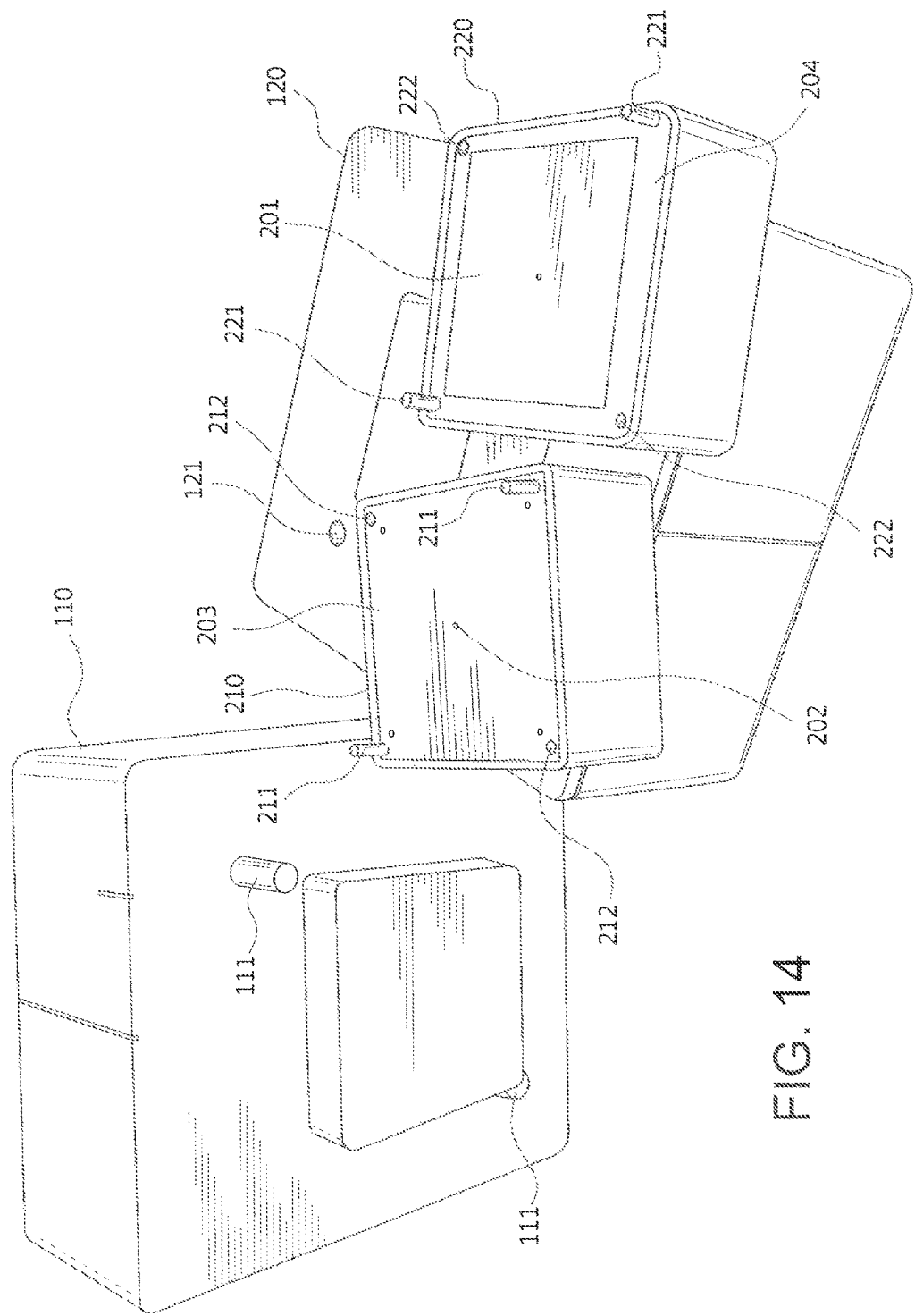
FIG. 14 is a perspective view of a verification phantom with a dosimetric insert in an open position according to one or more embodiments of the disclosed subject matter.

FIGS. 2 and 13 illustrate a first embodiment of the two insert pieces 210 and 220 in an opened position. FIG. 14 illustrates a second embodiment of the two insert pieces 210 and 220, with FIG. 14 also showing a dosimeter film insert 201 positioned on the upper surface of insert piece 220, so that when the two insert pieces 210 and 220 are assembled together, the film insert 201 rests there-between. The dosimeter film insert 201 can be used to determine the dose distribution or point dose value that the target/phantom is exposed to.

In an exemplary embodiment, one of the insert pieces 210 includes two pins 211 and two holes 212 positioned on surface 203 of the insert piece 210 so as to face corresponding holes 222 and pins 221 positioned on an opposing surface 204 of the second insert piece 220. The pins 211 and 221 can be attached to or secured to their respective insert pieces 210, 220 using any fastening or bonding mechanism, such as, but not limited to, nails, screws, etc. In one embodiment, the pins 211, 221 are glued to the insert pieces 210, 220 using an adhesive. To assemble the inner insert 200, the pins 211 of the first insert piece 210 can slide into the holes 222 of the second insert piece 220, and pins 221 of the second insert piece 220 can slide into the holes 212 of the first insert piece 210. The two insert pieces 210 and 220 are maintained in an assembled position by the friction between the pins 211, 221 and the surface of the holes 212, 222. The pins 211, 221 can be made of a plastic material, such as, but not limited to, polyvinyl chloride (PVC), and each can have a diameter of about 3 mm and a length of about 20 mm. The pins 211, 221 can also be made of a material that simulates the density of a tissue or a body organ, such as, but not limited to bone density. The corresponding holes 212, 222 also have a diameter of approximately 3 mm and a length of about 20 mm so as to allow insertion of the pins 211, 221 there-within and the assembly and connection of the two insert pieces 210 and 220 to each other through friction.

Figure 15:
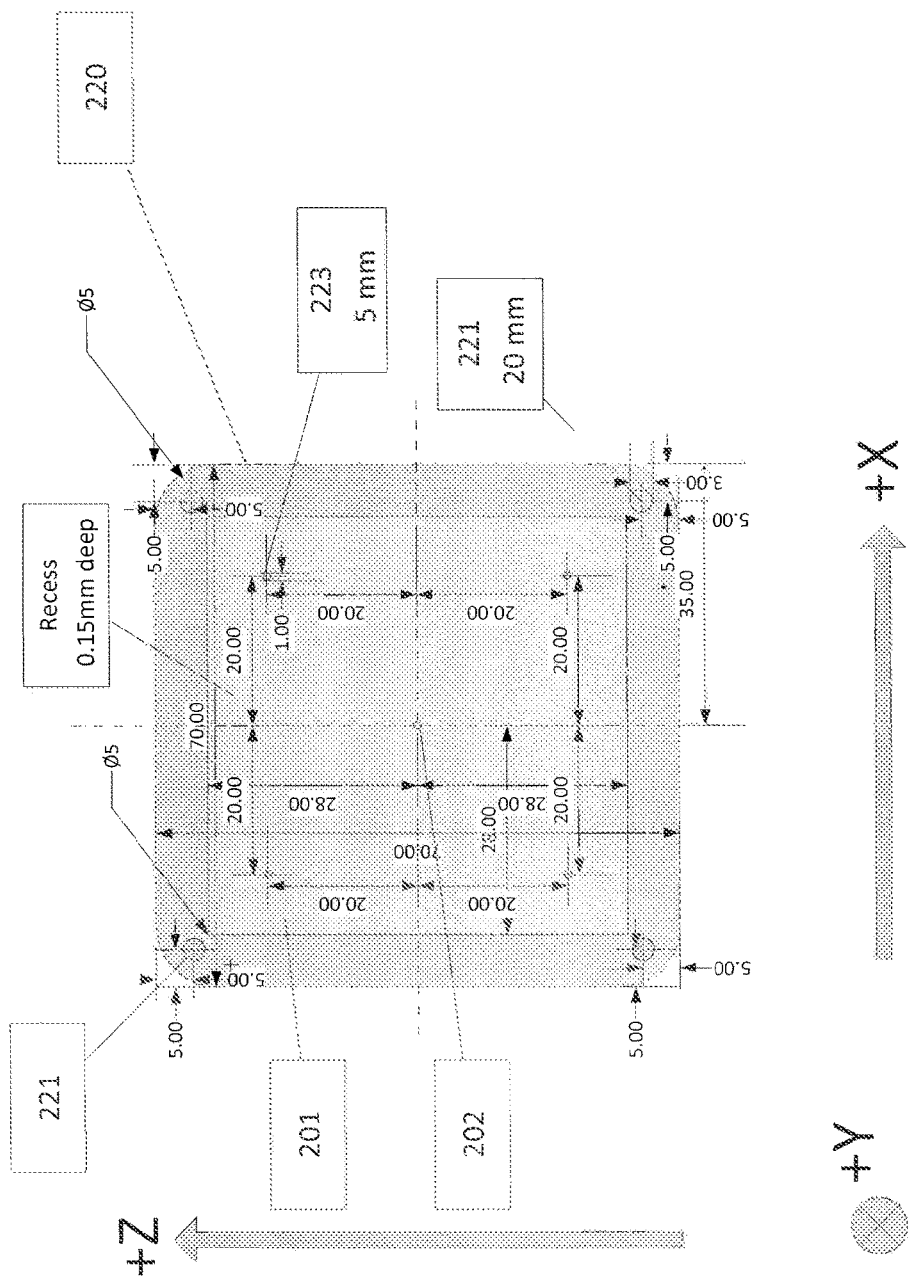
FIG. 15 is a plan view (coronal plane, anterior-posterior view) of a dosimetric insert in an open position with a film insert according to one or more embodiments of the disclosed subject matter.

FIG. 15 is a top view of an illustrative film insert 201 that can be used with the insert pieces 210, 220 shown in FIG. 14. FIG. 15 is showing dimensions and precise positions of the pins 221, holes 222, and film insert 201 for an exemplary embodiment. The film insert 201 receiving surface of the insert piece 210 is identical, except for the positions of the pins 211 and holes 212 on the surface 203. Each of the pins 221 can be positioned at approximately 5 mm from the corner edges of the insert piece 220, so that the center of the pin 221 located in the right corner of the insert piece 220 is positioned at (X=35 mm, Y=0 mm, Z=−30 mm) and the center of the insert pin 221 located in the diagonally opposed corner is positioned at (X=−35 mm, Y=0 mm, Z=30 mm) from the center of the phantom located at (X=0, Y=0, Z=0). The holes 222 are positioned similarly as the pins 221 in the remaining two corners of the insert piece 220. The pins 211 and holes 212 of the insert piece 210 are similarly located as the corresponding holes 222 and pins 221 on the insert piece 220. The locations, dimensions, and number of pins are exemplary, and any other locations, dimensions, and number of pins, may be used in order to fit the insert pieces 210, 220. The film insert 201 can be positioned in between the insert pieces 210, 220 using pins 211, 221. Alignment holes 202, 213, 223 can also be used to mark the film so that these markings are later seen in CT images used for dose planning, for example. The alignment hole markings form known points on the film plane, which helps to later align the film to the planning isocenter to determine the shift between measured dosimetric isocenter and planned dosimetric isocenter. In an exemplary embodiment, four alignment holes 223 are made in the insert piece 220, each positioned at a respective corner portion of the insert piece 220, so that the centers of the alignment holes 223 are each positioned approximately 15 mm from the respective edges of the insert piece 220, at the following locations relative to the center of the phantom: hole 1 at (X=20 mm, Y=0 mm, Z=−20 mm), hole 2 at (X=−20 mm, Y=0 mm, Z=−20 mm), hole 3 at (X=20 mm, Y=0 mm, Z=20 mm), and hole 4 at (X=−20 mm, Y=0 mm, Z=20 mm). The alignment hole 202 is positioned at (X=0, Y=0, Z=0). The holes 213 and 202 in the insert piece 210 are located at identical locations as in the insert piece 220. The locations, dimensions, and number of holes are exemplary, and any other locations, dimensions, and number of holes, may be used.

For better alignment and visualization of the film insert 201 relative to other elements of the insert piece 200 and the phantom 100, the alignment holes 202, 213, 223 can also include pins/pegs or any other mechanisms that can be inserted into one or more of the alignment holes 202, 213, 223 of one or both of the insert pieces 210, 220. In an embodiment, pins or pegs having 1 mm cross-sections and lengths of about 5 mm can be inserted into the alignment holes 202, 213, 223 so as to be flush with surfaces 203 and 204. The pins can be made of a plastic material that simulates a tissue or an organ of the body, such as, but not limited to the lung. When the insert pieces 210 and 220 are secured to each other through pins 211, 221, the dosimeter film insert 201 is securely positioned and aligned relative to the insert pieces 210, 220 and relative to the inner cubic insert 200. The insert piece surfaces 203 and 204 can also be slightly recessed so as to accommodate the film insert flush therebetween.

In some embodiments, the dosimetic insert 200 can also hold a centrally located marker, such as a steel or tungsten BB sphere marker in order to increase the contrast in MV/kV images. The film insert 201 can be a square film insert having a length of 56 mm on each side and a 0.3 mm thickness. To accommodate such a film insert 201 flush in between the two insert pieces 210, 220, the depth of each of the surface 203, 204 recesses is made to be about 0.15 mm. The films insert 201 can include any type of radiochromic films, including standard and/or high-sensitivity radiochromic films.

Figure 16:
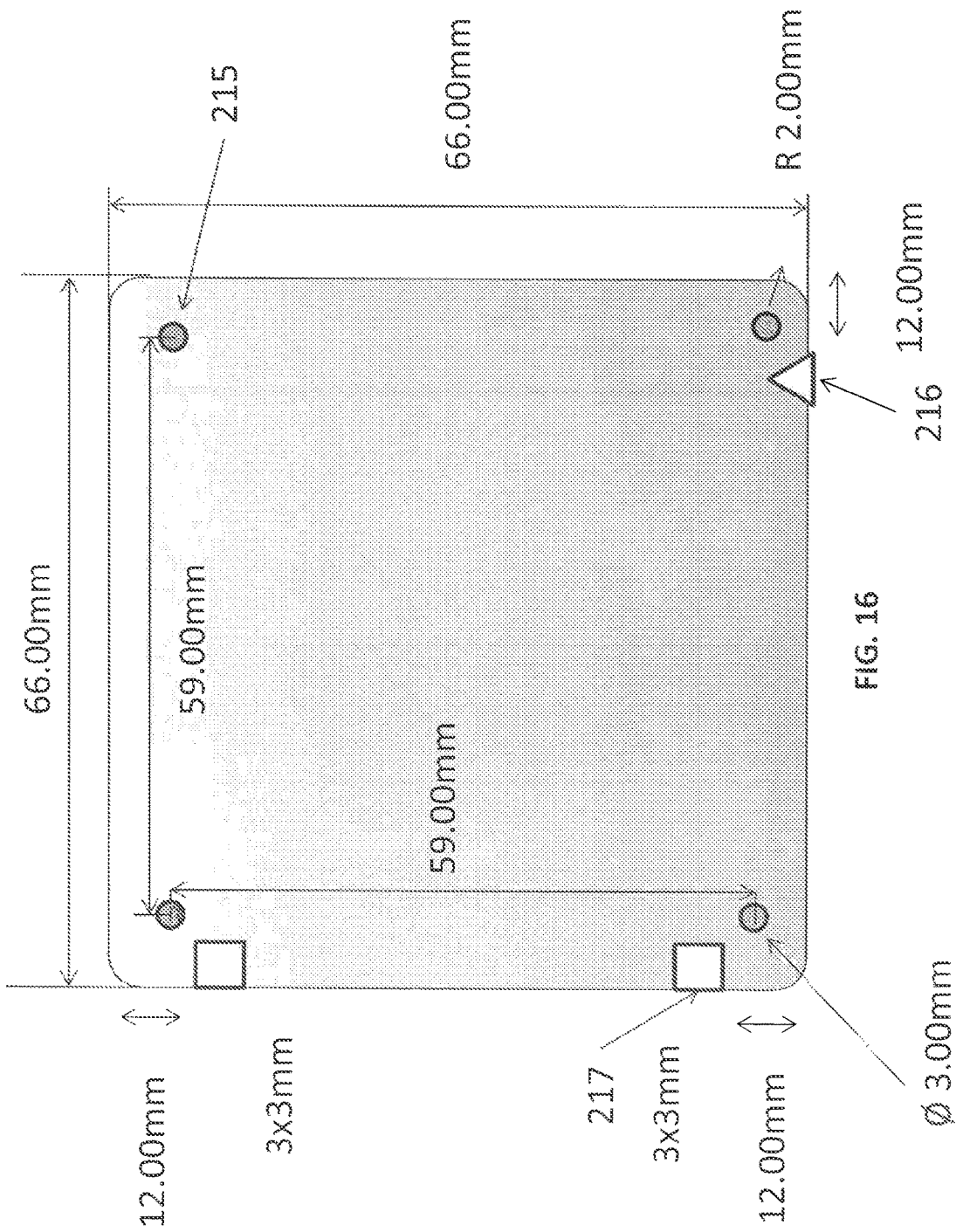
FIGS. 16-17 are plan views of film inserts for inserting into test phantoms according to one or more embodiments of the disclosed subject matter.

FIG. 16 shows an illustrative film insert 205 that can be used with the insert pieces 210, 220 shown in FIG. 13. The film insert 205 can have 66 mm long sides. The edges of the film insert 205 can be rounded to follow an arc having radius of about 2 mm to eliminate imaging artifacts. Film insert 205 can also include four circular cutouts 215 positioned at the four corners of the film insert 205. These cutouts 215 allow the pins 211 to hold and position the film insert 205 within the inner insert 200. Each of the circular cutouts 215 has a diameter of about 3 mm and is positioned so that its center is located approximately 3.5 mm from the edges of the film insert 205. The distance between adjacent circular cutouts is approximately 59 mm. The film insert 205 can also include other fiducial markers, such as an equilateral triangle-shaped cutout 216 having 3 mm long sides made along one of the sides of the film insert 205, as well as a plurality of square-shaped cutouts 217 having 3 mm sides made along another side of the film insert 205 to uniquely identify the film plane after the phantom 100 has been dismantled. The triangular cutout 216 can be positioned about 12 mm from the edge of the film insert 205 and two of the square-shaped cutouts 217 can each be positioned about 12 mm from corresponding edges of the film insert 205 at about 42 mm from each other. The films insert 205 can include any type of radiochromic films, including standard and/or high-sensitivity radiochromic films.

The dimensions and precise positions of the pins 221, holes 222, and film insert 205 is slightly different than the dimensions and positions of the film insert 201 in the insert piece 220 of the first embodiment. Each of the pins 221 can be positioned at diagonally opposed corners of the insert piece at approximately 4 mm from the corner edges of the insert piece 220. The holes 222 are positioned similarly as the pins 221 in the remaining two corners of the insert piece 220. The pins 211 and holes 212 of the insert piece 210 are similarly located as the corresponding holes 222 and pins 221 on the insert piece 220. The locations, dimensions, and number of pins are exemplary, and any other locations, dimensions, and number of pins, may be used in order to fit the insert pieces 210, 220.

The film insert 205 can be positioned in between the insert pieces 210, 220 using pins 211, 221. Alignment holes 202, 213, 223 can also be used to mark the film so that these markings are later seen in CT images used for dose planning, for example. The alignment hole markings form known points on the film plane, which helps to later align the film to the planning isocenter to determine the shift between measured dosimetric isocenter and planned dosimetric isocenter. In an exemplary embodiment, four alignment holes 223 are made in the insert piece 220, each positioned at a respective corner portion of the insert piece 220, so that the centers of the alignment holes 223 are each positioned approximately 9 mm from the respective edges of the insert piece 220. The holes 213 and 202 in the insert piece 210 are located at identical locations as in the insert piece 220. The locations, dimensions, and number of holes are exemplary, and any other locations, dimensions, and number of holes, may be used.

For better alignment and visualization of the film inserts 205 relative to other elements of the insert piece 200 and the phantom 100, the alignment holes 202, 213, 223 can also include pins/pegs or any other mechanisms that can be inserted into one or more of the alignment holes 202, 213, 223 of one or both of the insert pieces 210, 220. In an embodiment, pins or pegs having 1 mm cross-sections and lengths of about 5 mm can be inserted into the alignment holes 202, 213, 223 so as to be flush with surfaces 203 and 204. The pins can be made of a plastic material that simulates a tissue or an organ of the body, such as, but not limited to the lung. When the insert pieces 210 and 220 are secured to each other through pins 211, 221, the dosimeter film insert 205 is securely positioned and aligned relative to the insert pieces 210, 220 and relative to the inner cubic insert 200. The insert piece surfaces 203 and 204 can also be slightly recessed so as to accommodate the film insert flush therebetween.

The film insert 205 can be a square film insert having a length of 66 mm each side and a 0.3 mm thickness. To accommodate such a film insert 205 flush in between the two insert pieces 210, 220, the depth of each of the surface 203, 204 recesses is made to be about 0.15 mm. The films insert 205 can include any type of radiochromic films, including standard and/or high-sensitivity radiochromic films.

Figure 17:
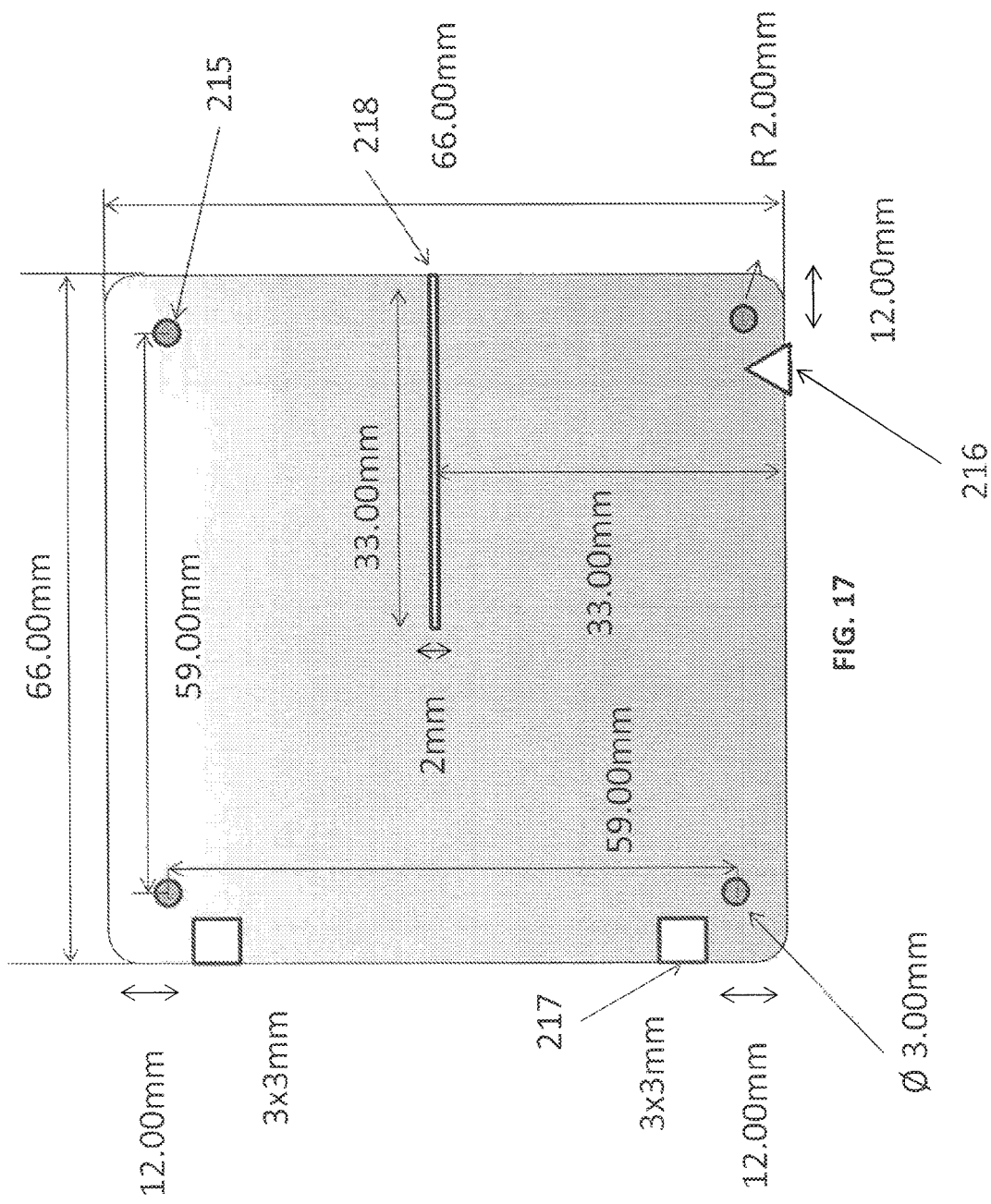

FIG. 17 illustrates another film insert 206 that can be used with the insert pieces 210, 220 of FIG. 13. The film inserts 206 can have sides 66 mm long. The edges of the film inserts 206 can be rounded to follow an arc having radius of about 2 mm to eliminate imaging artifacts. Film inserts 206 can also include four circular cutouts 215 positioned at the four corners of the film insert 206. These cutouts 215 hold and position the film insert within the inner insert 200 via the pins 211, 221. Each of the circular cutouts 215 has a diameter of about 3 mm and is positioned so that its center is located approximately 3.5 mm from the edges of the film insert 206. The distance between adjacent circular cutouts is approximately 59 mm. The film insert 206 can also include other fiducial markers, such as an equilateral triangle-shaped cutout 216 having 3 mm long sides made along one of the sides of the film insert 206, as well as a plurality of square-shaped cutouts 217 having 3 mm sides made along another side of the film insert 206 to identify uniquely the film plane after the phantom 100 has been dismantled. The triangular cutout 216 can be positioned about 12 mm from the edge of the film insert 206 and two of the square-shaped cutouts 217 can each be positioned about 12 mm from corresponding edges of the film inserts 206 at about 42 mm from each other. Each of the film inserts 206 can also include an elongated rod-shaped geometric cutout 218 having a diameter of about 2 mm and a length of about 33 mm. The rod-shaped cutout 218 can be made in a different side of the film insert 206 than where the triangular 216 and cubic cutouts 215 are made, so that its length extends along an axis which is perpendicular to the side of the film insert 206 where the square-shaped cutouts 217 are made. The rod-shaped cutout 218 extends about 33 mm from the side in which the triangular cutout 216 is made.

The number, shape, size, and positions of the geometric configurations in either of these films are only illustrative and any fewer or more geometric configurations, and different shapes, positions and sizes can be used. These geometric markings can be positioned to provide a reference position to the dosimeter film inserts held in the phantom 100 by the cubic insert 200. These geometric markings can be used to define a reference location and/or coordinate system so that the location of other features developed on the dosimeter films may be determined with respect to the radiation treatment device. When the phantom 100 is irradiated from a plurality of external radiation beam source positions, the radiation beams from the different positions provide image features (such as lines, or other marks) to the dosimeter films, which can be used to determine the trajectory of the respective radiation beams. These trajectories can then be used to determine an isocenter of the radiation treatment system in a coordinate system defined by the reference marks formed in the image. Additionally, the resultant dose distribution planned and irradiated can be used to determine the isocenter shift of the planned with respect to the measured 2D does distribution of the film.

Figure 18:
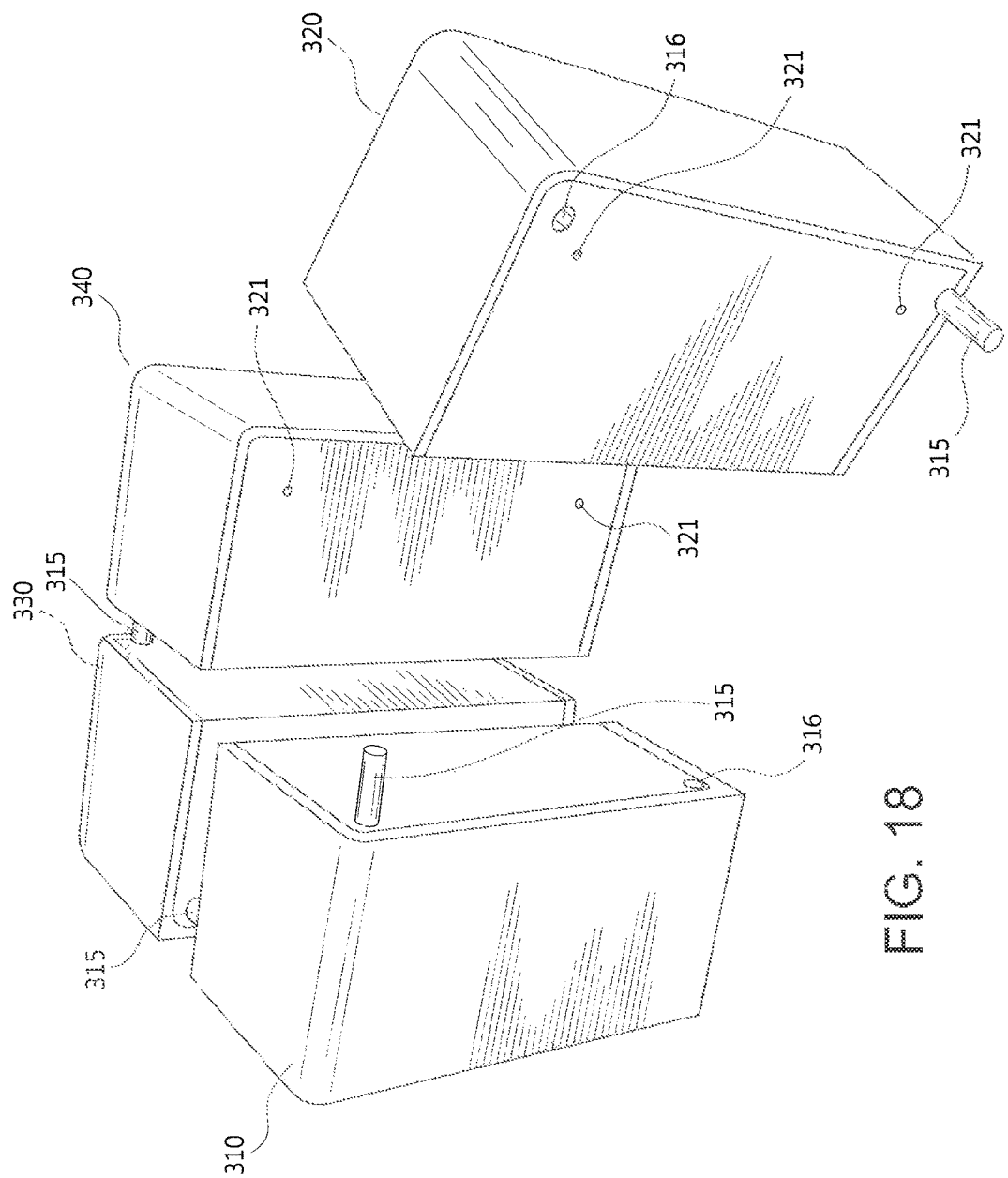
FIG. 18 is a perspective view of a dosimetric insert in an open position of a verification phantom according to one or more embodiments of the disclosed subject matter.

In an alternative embodiment, the inner cubic assembly insert 200 includes four separate rectangular insert pieces 310, 320, 330, and 340 which when assembled together form the inner cubic insert 200, as shown in FIG. 18. The inner insert 200 can be positioned inside the composite recess so as to nest within the composite recess when the two housing pieces 110, 120 are assembled together to form phantom 100' shown in FIG. 8. When the outer housing 130 is assembled together, the first and second insert pieces 310, 320 rest in the recess 113 of the first housing piece 110 and the third and fourth insert pieces 330, 340 rest in the recess 123 of the second housing piece 120. The insert pieces 310, 320, 330, and 340 can be formed of a material such as polyurethane having a density of 1.05 g/cm$^3$, for example. However, the insert pieces 310, 320, 330, and 340 can be made of any other material having different densities which can represent different densities of different organs and media of the human body which the radiation beam of the radiation treatment device may pass through.

FIG. 18 illustrates the four insert pieces 310, 320, 330, 340 in an opened position. In one embodiment, two (2) film inserts can be positioned between the four insert pieces 310, 320, 303, and 340 before assembling the pieces 310, 320, 330, and 340 together, so that, when assembled, the combined film inserts rest between the assembled insert pieces 310, 320, 330, 340 in two orthogonal planes. The two film inserts will rest in the inner cubic insert 200 and the phantom 100' as shown in FIG. 8. The first and second film inserts can be film inserts as shown in FIG. 17. When two crossed-film inserts 206 are used in the inner insert 200, the rod-shaped cutouts 218 in each film insert 206 interlock with each other to form a crossed-film insert by sliding one film insert into the rod-shaped cutout of the other film insert. The first and second film inserts 206 can slide into each other (i.e., mate with each other) via their respective rod-shaped cutouts. When the two film inserts are mated with each other via their respective rod-shaped cutouts, the two film inserts are interlocked to form a dual-crossed film insert, with the first film insert resting in a plane which is perpendicular to a plane in which the second film insert rests. The two film inserts are positioned so as to slice through the center of the inner insert 200 in orthogonal planes. Since the film inserts slice through two-dimensional planes within the insert 200, the delivered dose image developed thereon will capture two-dimensional slices of the actual dose delivered. Thus, treatment planning software can also be used to determine calculated doses that should be delivered along these planes. The film inserts 206 can include any type of radiochromic films, including standard and/or high-sensitivity radiochromic films.

The first and second insert pieces 310 and 320 each include pins 315 and holes 316 positioned on their inner surfaces which face each other and the other two inserts 330, 340, so that the first and second insert pieces 310 and 320 can be assembled to each other, as well as to insert pieces 330, 340 through the pins connected/attached to their respective inner surfaces. In the exemplary embodiment pins can be used to securely assemble the insert pieces to each other by friction between the pins and the surfaces of the corresponding holes. The pins 315 can be made of a plastic material, such as, but not limited to, polyvinyl chloride (PVC), and each can have a diameter of about 3 mm and a length of about 20 mm. The pins 315 can also be made of materials that simulate bone density. The pins 315 can be securely attached to their corresponding insert pieces by gluing the pins onto the insert piece surfaces, for example. However, other securing/connecting/attaching methods may also be used. The corresponding holes can also have a diameter of approximately 3 mm and a length of about 5 mm so as to allow insertion of the pins therewithin and assembly and connection of the four insert pieces 310, 320, 330 and 340 to each other through friction.

When the insert pieces 310, 320, 330, and 340 are assembled, the dual crossed film inserts are securely positioned and aligned relative to the inner insert 200. The film inserts are precisely cut to fit into the insert 200 so that the positions of the film inserts within the insert 200 are precisely known. The insert piece surfaces can also be slightly recessed so as to accommodate the film inserts flush therebetween. Due to the precise positioning of the dosimeter dual-crossed film inserts within the cubic inner insert 200 and within the phantom 100', accurate three-dimensional translational and rotational alignment validation can be provided.

In an alternative embodiment, the inner insert 200 can be formed of three different insert pieces with one insert piece (i.e., first insert piece) including a slit having a specific width across substantially a middle portion thereof so as to allow insertion of a portion of a first film insert therein. When inserted in the slit, the portion of the film insert is resting within the first insert piece and the rest of the film insert is resting outside of the first insert piece in a plane which is orthogonal to the surface of the first insert piece. A second film insert can be positioned on the upper surface of the first insert piece, so that the first and second film inserts form a dual crossed film insert when the insert pieces are assembled. The other two insert pieces (second and third) are positioned on the first insert piece so as to hold the first film insert there-between.

In an exemplary embodiment, the first and the second film inserts are film inserts as shown in FIG. 17.

Figure 19:
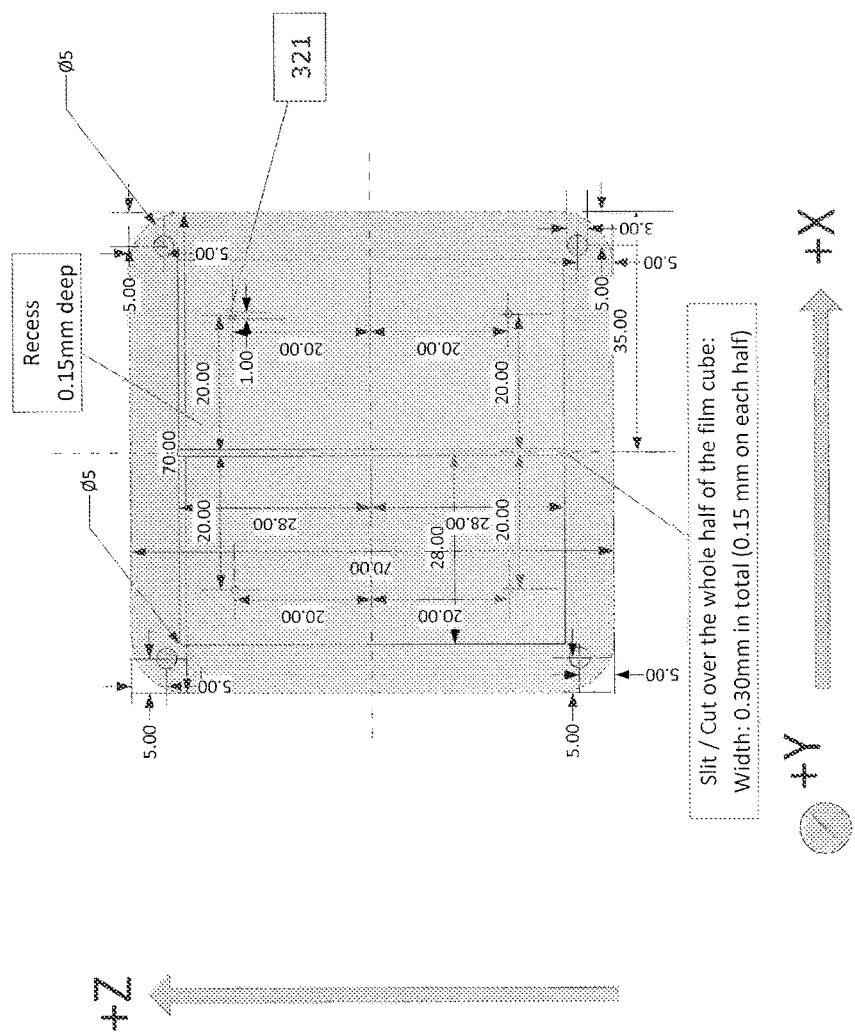
FIG. 19 is a plan view (coronal plane, anterior-posterior view) illustrating a film insert in a verification phantom according to one or more embodiments of the disclosed subject matter.
Figure 20:
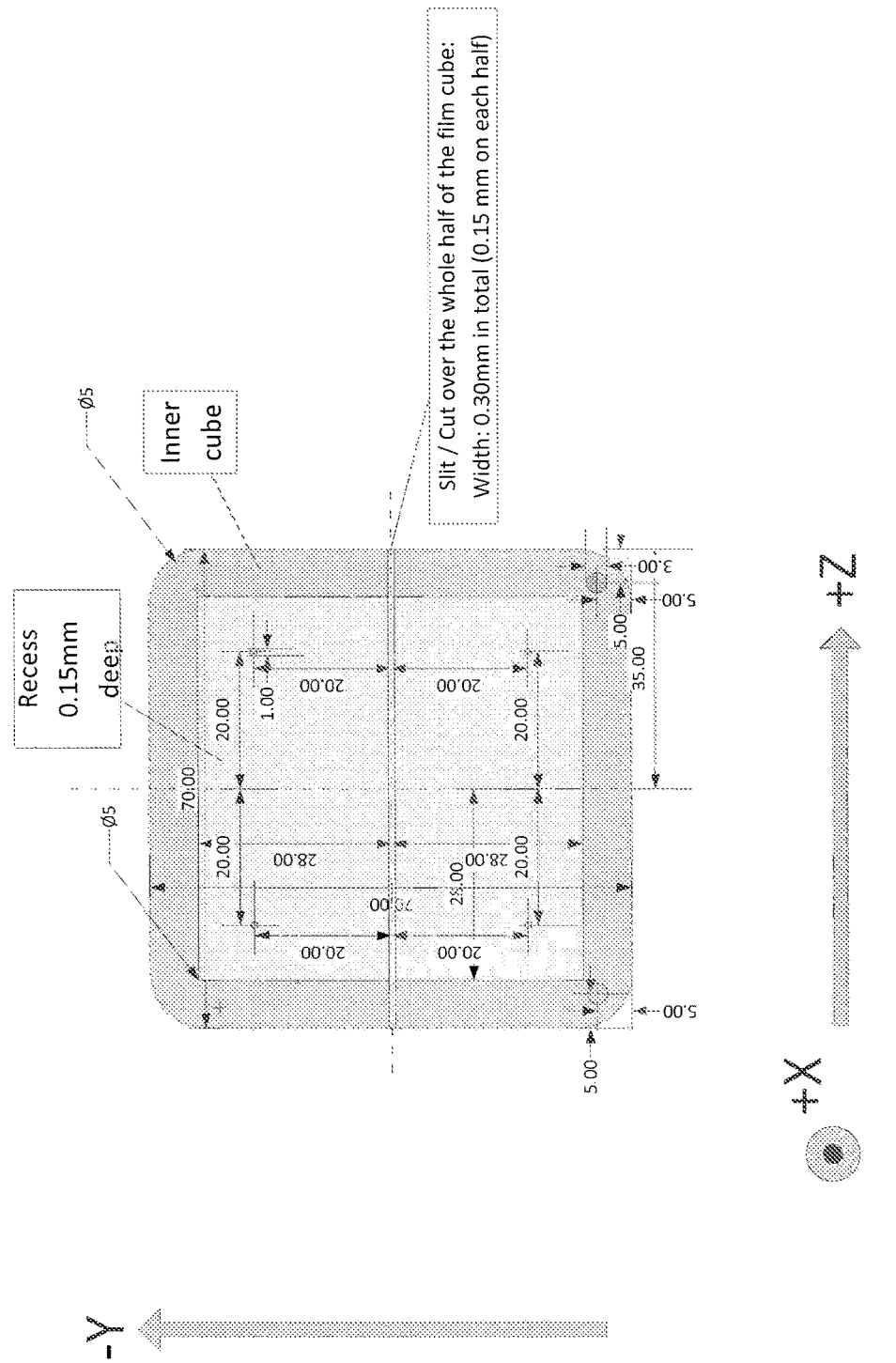
FIG. 20 is a plan view (sagittal plane, left-right view) of the film insert of FIG. 19.

In another embodiment, the first film insert can be a film insert as shown in FIG. 16 and the second film insert is made up of two film insert pieces, located on either side of the slit in the first insert piece. FIGS. 19 and 20 illustrate top views of the second film insert pieces. The film insert pieces each can have a side 28 cm long and another side which is 56 mm long, respectively, so as to leave a slit/cut having a width of 0.3 mm where the two film insert pieces meet. The film insert pieces can be positioned on the insert piece using alignment holes 321. In an exemplary embodiment, four alignment holes 321 are made in the insert piece, each positioned at a respective corner portion of the insert piece, so that the centers of the alignment holes 321 are each positioned approximately 15 mm from the respective edges of the insert piece 310, at the following locations relative to the center of the phantom 100: hole 1 at (X=−20 mm, Y=0 mm, Z=−20 mm), hole 2 at (X=−20 mm, Y=0 mm, Z=20 mm), hole 3 at (X=20 mm, Y=0 mm, Z=−20 mm), hole 4 at (X=20 mm, Y=0 mm, Z=20 mm).

For better alignment and visualization of the film inserts relative to other elements of the insert piece 200 and the phantom 100, the alignment holes 321 can also include pins/pegs or any other mechanisms that can be inserted into one or more of the alignment holes 321 of the insert piece. In an embodiment, pins or pegs having 1 mm cross-sections and lengths of about 5 mm can be inserted into the alignment holes 321 so as to be flush with the insert piece. The pins can be made of a plastic material that simulates a tissue or an organ of the body, such as, but not limited to the lung.

When the insert pieces are assembled, the dosimeter film inserts are securely positioned and aligned relative to the insert pieces and relative to the inner cubic insert 200 to form a dual crossed film insert. Due to the precise positioning of the dosimeter film inserts within the cubic inner insert 200 and within the phantom 100', accurate three-dimensional translational and rotational alignment validation can be provided.

In an alternative embodiment, the cubic insert 200 can be made of one single piece and can include a plurality of groves, each being able to accommodate a respective film insert, such that when the film inserts are inserted into the respective groves, the plurality of film inserts are positioned in a stacked configuration. The cubic insert 200 can further include additional fiducial markers so that the position of each film relative to the cubic insert 200 is precisely known. Three-dimensional (3D) dosimetry can be achieved with the phantom including such a cubic insert 200. In another embodiment, the stack of films in the cubic insert 200 is stacked in such a way as to achieve a 2½D dosimetry.

Instead of, or in combination with the film inserts, the cubic insert 200 can also include thermoluminescent dosimeters (TLD) for dose distribution measurements. In this case, instead of, or in combination with reading the optical density (blackness) of the film inserts, the amount of light released versus the heating of the individual pieces of thermoluminescent material can also be measured. The "glow curve" produced by this process is then related to the radiation exposure. The point dose measurement is determined based on this glow curve.

Alternatively, instead of, or in combination with the film inserts, the cubic insert 200 can also include optically stimulated luminescence (OSL) dosimeter films for dose distribution measurements. In this case, instead of, or in combination with reading the optical density (blackness) of the film inserts, photons are detected using a photomultiplier tube. The signal from the tube is then used to calculate the dose that the material had absorbed.

Alternatively, instead of or in combination with using the film inserts, the cubic insert 200 can host a dosimetry gel container for 3D dose distribution measurements.

By precisely positioning dosimetric film inserts, such as, gel, film, TLD and/or OSL dosimeters in multiple planes in the interchangeable cubic insert 200, three-dimensional (3D) imaging of radiation dose distribution can be achieved, which then allows determining the absolute or relative dose distribution or point distribution dose values. Knowing the absolute or relative dose distribution or point distribution dose values allows determining the center of the dose distribution or dose volume/area parameters to be compared to the calculated absolute or relative dose distribution.

In order to determine dose distribution using the phantom 100, 100' with the dosimeter film inserts, an imaging method may be used wherein the radiation source (e.g., X-ray source) of the radiation treatment system emits radiation beams onto the phantom 100, 100'. Subsequently, the radiation source is moved to one or more positions to take aim at the inner insert 200 of the phantom 100, 100'. From each position, the radiation source emits a radiation beam along a trajectory passing through the inner insert 200 and impinging upon the dosimeter film inserts to deliver prescribed doses of radiation per the treatment plan. In response to the radiation beams, the dosimeter film inserts are exposed and an exposure image or delivered dose image is developed on the dosimeter film inserts. The insert 200 can then be removed from the phantom 100, 100' opened, and the dosimeter film inserts removed for analyzing. By analyzing the shape, size, position, and/or optical density (amount of exposure represented by the shading on the film) of the exposure images on the dosimeter film inserts, alignment and/or calibration of the radiation source can be validated or a misalignment/invalid calibration exposed.

It will be appreciated that the phantom described herein can measure relative and absolute dose distribution due to its combination of various dosimeters in a single dosimetric insert. It will also be appreciated that the phantom described herein provides nearly identical marker (BB sphere) contrast in kV and MV projection images due to the optimized material composition of the markers (BB spheres) within the phantom, which allows artifact free CT and CBCT imaging of the embedded markers (BB spheres).

It will further be appreciated that because a variety of materials with different densities are used the phantom described herein, intensity variations result within X-ray, CT, CBCT, DTS images used in manual and automatic image registration algorithms, and therefore, the phantom can be used for the verification of the gantry and collimator rotation angle, jaw and MLC based field size, as well as for treatment couch shifts and rotations, for example.

By emitting multiple radiation beams from different positions onto the phantom 100, 100', multi-dimensional alignment validation can also be achieved, such as, but not limited to, three-dimensional translational alignment validation, and three-dimensional translational and rotational alignment validation (roll, pitch, yaw), which includes validating the ability of the radiation treatment system and the patient positioning system to achieve accurate translational/rotational placement of the phantom 100, 100' at the preset position and the ability of the radiation source to arrive at its translational/rotational preset position.

The reference indicia, fiducial markers, and/or any other marks, such as the geometric marks on the film and the housing, and the cross-shaped hairline marks, precisely positioned in or on the phantom 100, 100' provide a reference position to the dosimeter film inserts held in the phantom 100, 100' by the cubic insert 200. These marks being provided by materials or coatings that can generate an optically or electronically detectable image on the film inserts will generate such detectable images on the film inserts when exposed to the radiation beams. When the phantom 100, 100' with the inner insert 200 is irradiated with the radiation beam, these markers generate different patterns on the film inserts. The patterns may be visible after the film inserts are developed to create a digitized image. These marks can be used to define a reference location and/or coordinate system so that the location of other features developed on the dosimeter films may be determined with respect to the radiation treatment device. When the phantom

100, 100' is irradiated from a plurality of external radiation beam source positions, the radiation beams from the different positions provide image features (such as lines, or other marks) to the dosimeter films, which can be used to determine the trajectory of the respective radiation beams. These trajectories can then be used to determine an isocenter of the radiation treatment system in a coordinate system defined by the reference marks formed in the image. These markings can also be used to calibrate a laser system to the image-based treatment machine isocenter validated using phantom 100, 100'.

Figure 22:
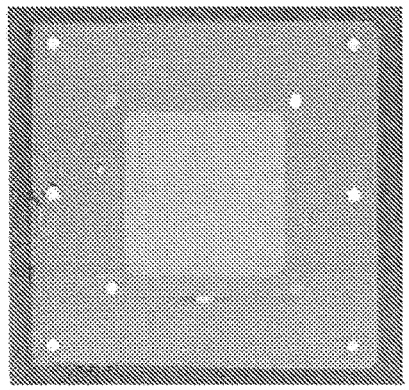
FIG. 22 shows a CT slice showing a central plane of a verification phantom according to one or more embodiments of the disclosed subject matter.
Figure 23:
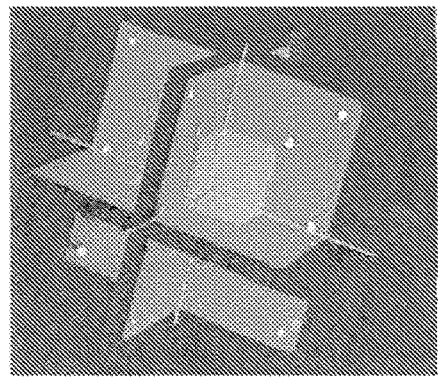
FIG. 23 shows a 3D view with two orthogonal CT planes of a verification phantom according to one or more embodiments of the disclosed subject matter.

Since the phantom 100, 100' includes precisely positioned fiducial markers, the phantom 100, 100' is also optimal for isocenter determination, verification, and calibration using imaging methods, such as but not limited to X-ray imaging methods. In an exemplary embodiment, to determine isocenter alignment using imaging methods, the phantom 100, 100' can first undergo a CT scan using a clinical simulator to generate images of the phantom 100, 100'. FIGS. 22 and 23 illustrate a plan view and a 3D view with two orthogonal planes, respectively, of images so obtained. The images show the fiducial markers, such as the BB markers, the transponders, pins, density inserts, etc., as well as the film insert of the phantom 100, 100'. The images so obtained can be exported to a treatment planning system where the insert 200 can be contoured and the isocenter placed at its centroid based on the alignment holes visible in the CT scan. The phantom can also be tailored for generating MRI images. Then the phantom 100, 100' can be securely attached to a patient support in a fixed position aligned with a set or marks, such that the axis of the phantom 100, 100' is parallel to the rotational axis of the gantry.

Figure 24:
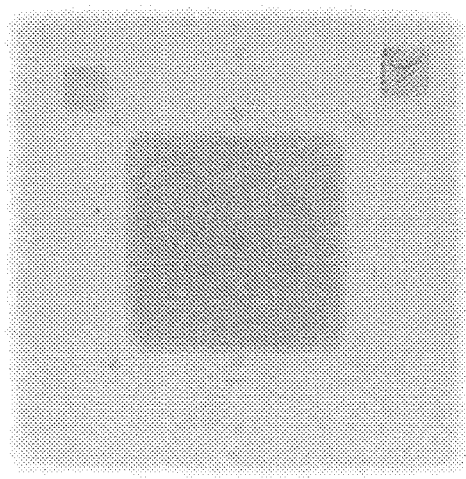
FIG. 24 is a kV image of a verification phantom according to one or more embodiments of the disclosed subject matter.
Figure 25:
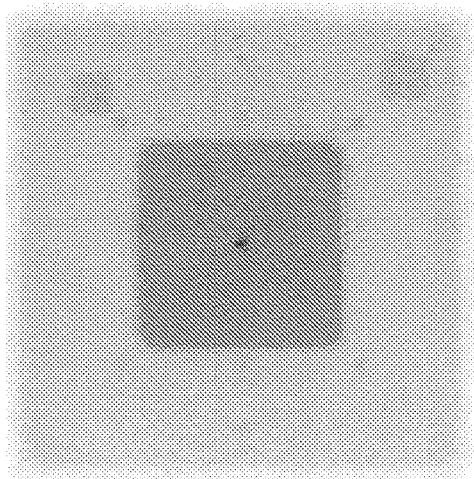
FIG. 25 is a MV image of a verification phantom according to one or more embodiments of the disclosed subject matter.

The radiation treatment system is then used to generate a set of images of the phantom 100, 100' at a plurality of gantry angles. The generated images will include the images of the fiducial markers, such as the BB sphere markers, density inserts, alignment pins, transponders, and any other additional markers used in the phantom 100, 100'. FIGS. 24-25 are exemplary images of the phantom obtained using a kilovoltage (kV) X-ray source (FIG. 24), and a megavoltage (MV) X-ray source (FIG. 25). Both images show the inset cube 200, BB markers, density inserts, the three transponders, alignment pins, and letter marking. After the images are obtained, a processing system determines the position of the first generated image (e.g., the image generated at the first gantry angle) and subsequently, the positions of the fiducial markings in the image. The processing system can next form a one-to-one correspondence between the projections of each of the fiducial markers in the first generated image and the fiducial markers themselves by, for example, determining a possible orientation of the phantom 100, 100' that could produce the arrangement of the fiducial markers in the image, using various determination techniques. The processing system can then determine the positions of the fiducial markers in all subsequent images in the set. After the positions of the fiducial markers at all prescribed gantry angles have been obtained, the processing system can determine the actual position of the gantry at each prescribed gantry angle, as well as the distance between the radiation source and the detector used in the system. Various determination techniques can be used for such purpose.

After the positions of the gantry at all prescribed gantry angles have been determined, the processing system can determine the coordinate of the geometric center of the phantom 100, 100' at each prescribed gantry angle. After the coordinate of the geometric center of the phantom 100 has been determined, the geometric center of the phantom 100, 100' can be projected onto a 2D image frame for each of the prescribed angles. The projected position of the center of the phantom 100, 100' is then compared with a center of a projected circle in the image for each of the prescribed gantry angles to determine/verify the actual isocenter. If the projected position of the center of the phantom 100, 100' is at, or is within prescribed distance from the center of the projected circle in at least two of the generated images, then the initial expected isocenter is determined to be the actual iscocenter of the treatment system. Otherwise, the initial expected isocenter position can be adjusted based on the difference. After the positions of the gantry at all prescribed gantry angles have been determined, the processing system can also determine the position and orientation of the gantry as well as one or more geometric parameters based on the determined positions of the gantry. Exemplary methods of determining the isocenter as well as one or more geometric parameters of a treatment system are described in detail in U.S. Pat. Nos. 7,844,094, 8,198,579, and are incorporated herein by reference in their entireties.

The phantom 100, 100' is also compatible with the so called unknown target point method, which is used in stereotactic treatments where a stereotactic co-ordinate system is used (e.g., BRW or Leksell co-ordinate system). In such a method, the phantom 100, 100' is used without aligning the target point or isocenter accurately to the stereotactic co-ordinate system. Instead, the target point is defined based on pre-treatment imaging, such as, but not limited to CT and MRI imaging. After the definition of the target point or isocenter, the dose distribution is planned and applied to the phantom to determine the offset between planned and achieved target point.

Since the phantom 100, 100' also includes precisely positioned transponders, the phantom 100, 100' is also optimal for isocenter determination, verification, and calibration using a Calypso system. In an exemplary method, the electromagnetic transponders, in the phantom 100, 100' can be used to communicate with Calypso localization systems using radiofrequency waves. The Calypso system is an electromagnetic, transponder-based, target localization and monitoring system, including an electromagnetic array which contains an energy source that can excite the transponders and receivers that detect each transponder's frequency to determine its location coordinates. Each of the transponders transmits a unique non-ionizing radiofrequency signal to the array, generating position and motion information about the target in which it is imbedded. The transponder's location is subsequently correlated to the treatment or machine isocenter through optical reflectors on the detector. A user interface can display the positional information both inside and outside of the treatment room. The system can also be multiplexed so that multiple transponders tuned at different frequencies can be discretely detected. The electromagnetic transponders and the Calypso system can also provide target localization and monitoring during radiation treatment delivery. During radiation treatment, the transponders and the Calypso system can provide the clinician continuous, real-time monitoring of the target and can alert the clinician when the target is outside of acceptable boundaries due to organ motion, thereby enabling corrections during the treatment delivery.

Since the markings, transponders, and density inserts are formed of materials which allow them to be optimally embedded into the phantom 100, 100' and thus, the outer surface of the phantom 100, 100' is also optimal for optical surface monitoring. Optical surface monitoring can be used as a verification system for patient setup and correction. In an exemplary embodiment, the phantom 100, 100' can be exposed to a laser-based surface scanning system for patient setup and verification and correction. For example, the phantom 100, 100' can be exposed to a 3D laser imaging system to scan its surface with laser light. The 3D laser imaging system can use lasers mounted on the radiation treatment system or the ceiling of the room that houses the radiation treatment unit to irradiate the surface of the phantom 100, 100' with laser light, and a camera positioned to capture and record the reflections of the projected laser lines. The 3D laser imaging system can then reconstruct a 3D surface model of the phantom/mimicked patient/organ/target volume. The actual position of the target is then compared with that of a reference image, which can be acquired either with the imaging system, or it may be generated by contouring the skin in the treatment planning CT. By comparing the two surface models, a setup correction can be calculated and used to correct the setup of the patient during radiation treatment.

Figure 21:
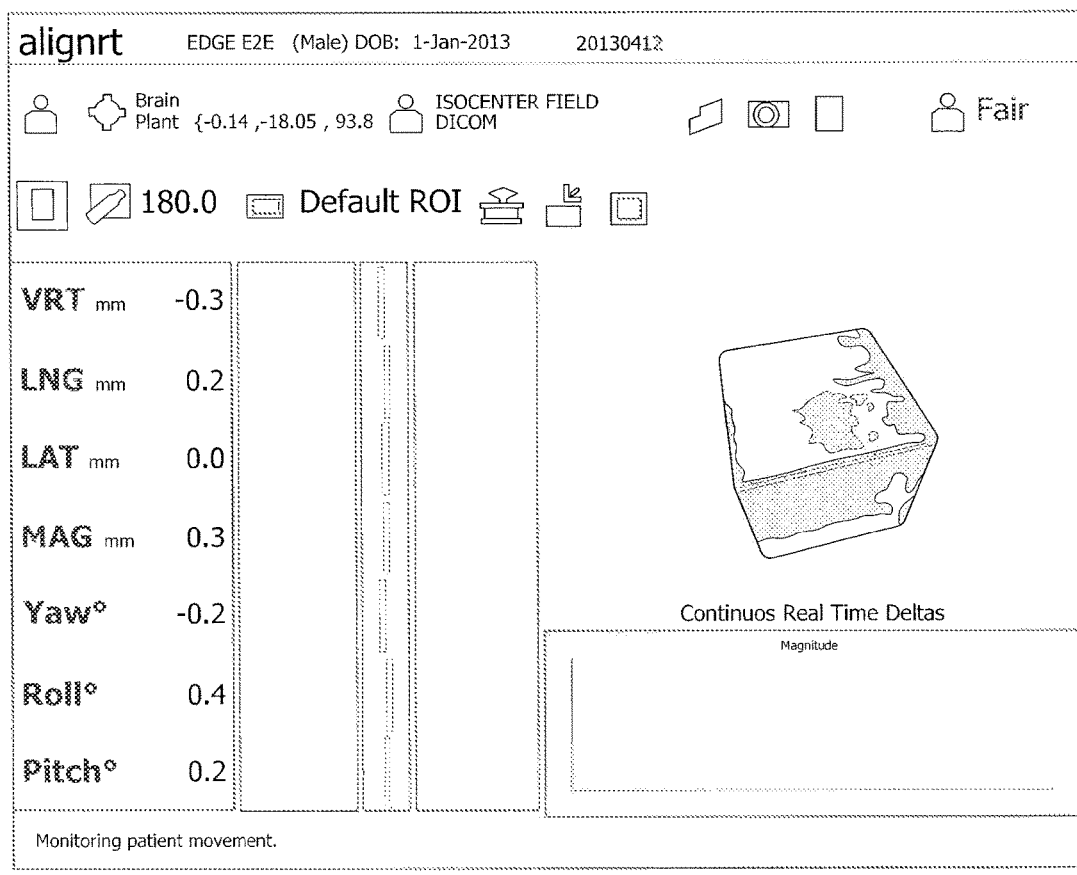
FIG. 21 is a screen shot of an optical surface detection software where the detected and reference phantom surface is shown together with translations and rotations to match both surfaces.

Although a laser-based surface scanning system has been described, any other optical surface measurement systems and methods, such as, but not limited to, an ultrasound-based optical surface measurement systems and methods can be used. Alternatively, any distance measurement device or any other localization device can also be used in order to provide an independent channel of position feedback, such as, but not limited to system as shown in FIG. 21, which enables continuous non-invasive real-time patient motion and respiratory tracking in 3D. This is particularly advantageous in situations where other detection systems may not work due to geometrical constraints.

It will be appreciated that the phantom described herein has the advantage of providing simultaneous position verification using a variety of positioning systems, such as imaging (X-ray, for example), optical surface detection (laser, ultrasound, etc. for example), and electromagnetic navigational system (Calypso monitoring, for example) in a single phantom. It will also be appreciated that the phantom can also be used to verify shifts and rotations of the phantom which have been determined by the use of the imaging, optical, and navigational monitoring systems. The phantom can also be used on a motion stage for Calypso, optical surface monitoring, and/or X-ray based motion determination including dosimetric verification of gated, MLC, or treatment couch compensated radiation treatments.

It will also be appreciated that the phantom described herein can be used as an end-to-end test phantom in the field of stereotactic radiation treatments to provide a combination of imaged-based, optical surface based, and navigational (Calypso, for example) based positioning to determine the uncertainty of each of these systems and to position the phantom to the combined center.

Figure 26:
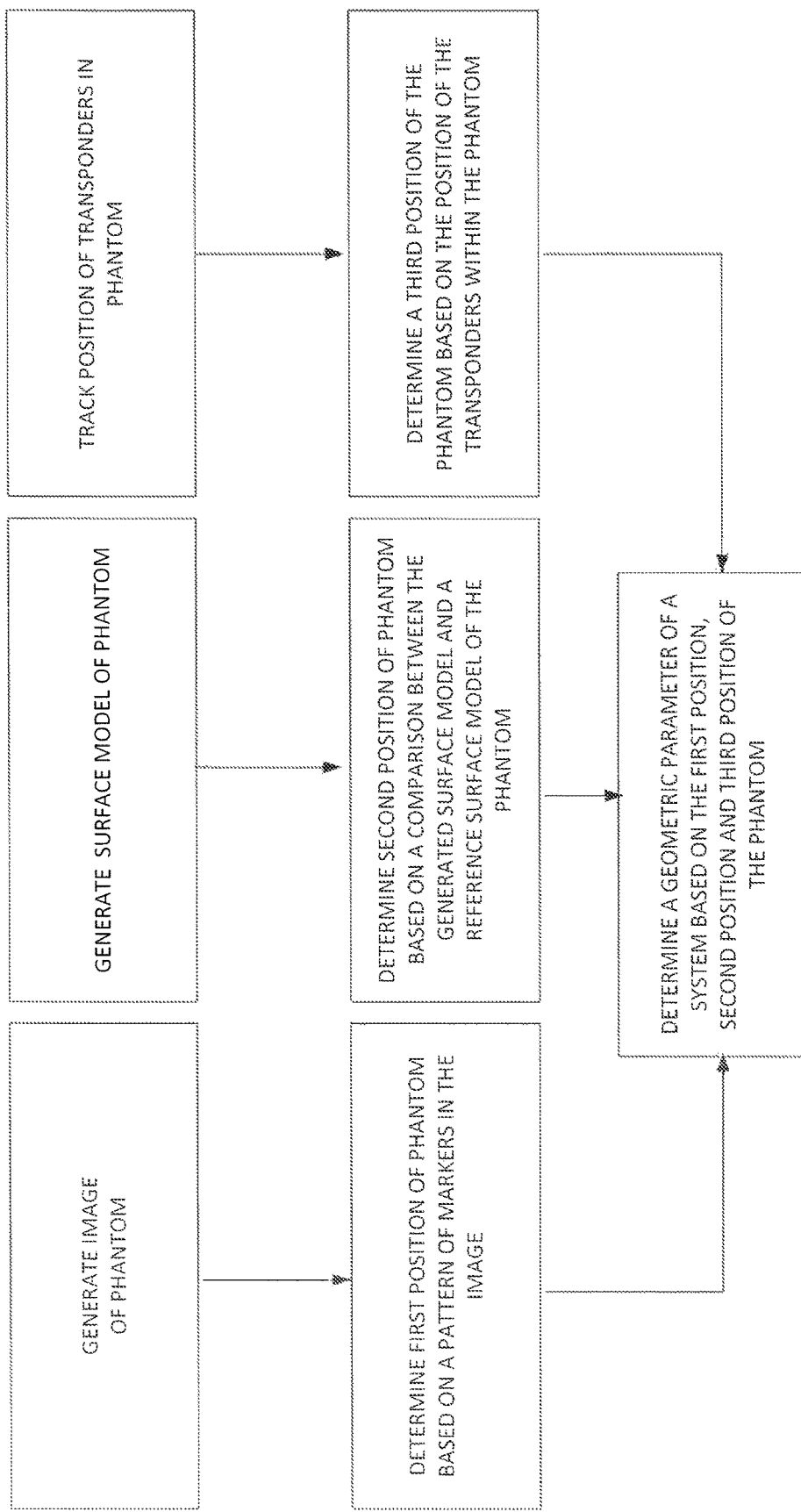
FIG. 26 is a flow chart illustrating a process for performing quality assurance check on a radiation treatment delivery system using a verification phantom according to one or more embodiments of the disclosed subject matter.

For example, as shown in FIG. 26, the phantom 100, 100' can be simultaneously exposed to an imaging system to generate an image of the phantom, from which a first position of the phantom is determined based on the pattern of markers in the image. At the same time, a surface model of the phantom can be generated, using an optical surface imaging method. A second position of the phantom can be determined based on a comparison of the generated surface model and a reference surface model. The phantom can also be continuously monitored using a Calypso monitoring system, and a third position of the phantom can be determined based on the monitored position of the transponders embedded in the phantom. Based on the first, second, and third determined positions, a combined center for the phantom can be determined. The phantom, and ultimately the patient, can then be positioned at the combined center for the treatment system. A geometric parameter, such as, but not limited to, the treatment machine isocenter, and/or the uncertainty of each of these imaging and monitoring systems can also be determined based on the phantom positions determined using the different monitoring systems.

In embodiments, one or more images can be generated to determine the first position of the phantom. The one or more images can include images obtained using kV, MV, CT, CBCT, SPECT, PET, MRI, or any other applicable imaging systems and methods.

In one example, the phantom 100, 100' can be simultaneously exposed to an X-ray imaging system to generate an X-ray image of the phantom, from which a first position of the phantom is determined based on the pattern of markers in the X-ray image as discussed above. At the same time, a surface model of the phantom can be generated, using an optical surface imaging method. A second position of the phantom can be determined based on a comparison of the generated surface model and a reference surface model. The phantom can also be continuously monitored using a Calypso monitoring system, and a third position of the phantom can be determined based on the monitored position of the transponders embedded in the phantom. Based on the first, second, and third determined positions, a combined center for the phantom can be determined. The phantom, and ultimately the patient, can then be positioned at the combined center for the treatment system. A geometric parameter, such as, but not limited to, the treatment machine isocenter, and/or the uncertainty of each of these imaging and monitoring systems can also be determined based on the phantom positions determined using the different monitoring systems.

In embodiments, the X-ray image is generated using a kV, MV, CT, or CBCT imaging system.

Figure 27:
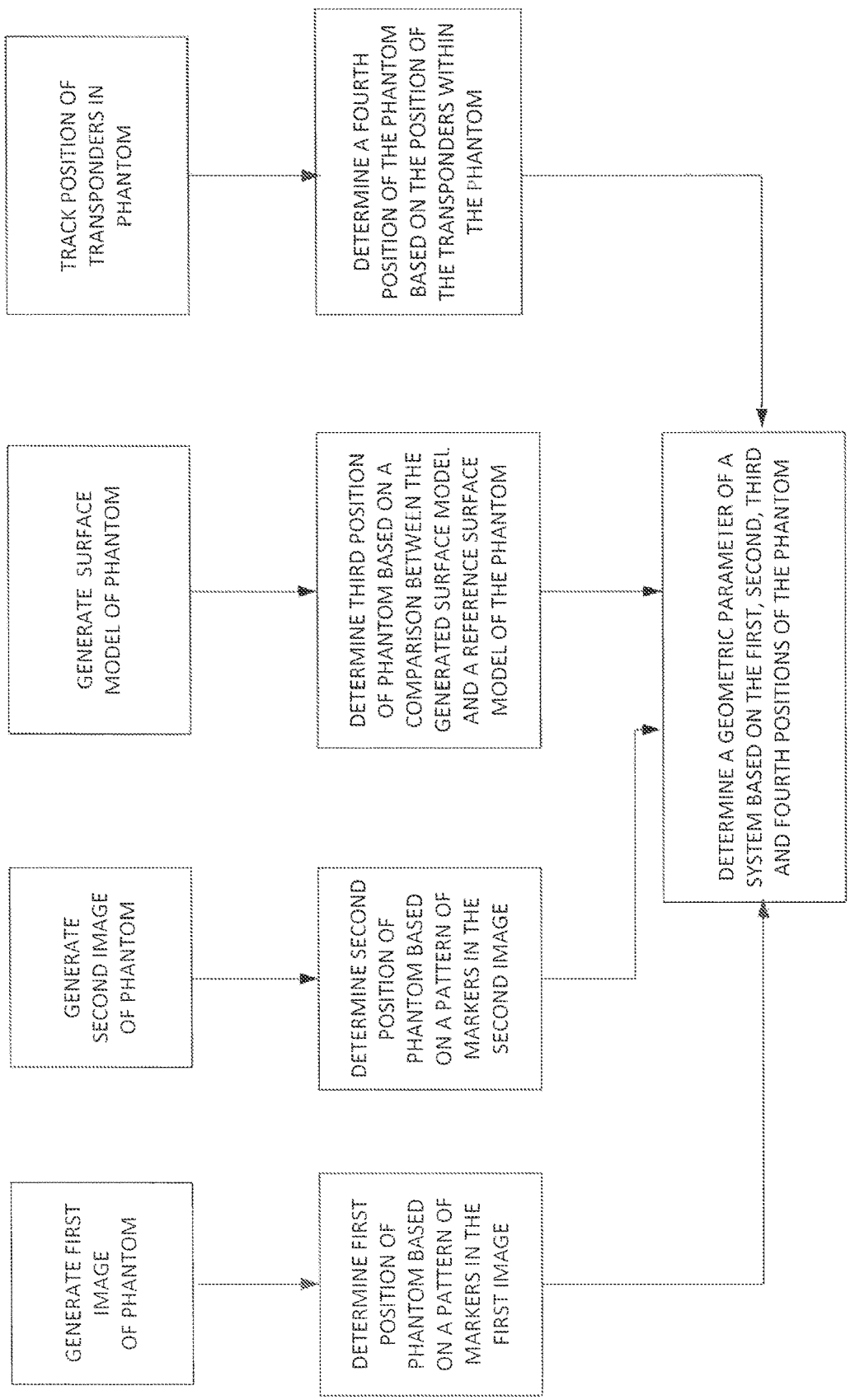
FIG. 27 is a flow chart illustrating a process for performing quality assurance check on a radiation treatment delivery system using a verification phantom according to one or more embodiments of the disclosed subject matter.

In other embodiments, as shown in FIG. 27, the phantom 100, 100' can be exposed to a first imaging system to generate a first image of the phantom, from which a first position of the phantom is determined based on the pattern of markers in the first image. The phantom 100, 100' can also be exposed to a second imaging system to generate a second image of the phantom, from which a second position of the phantom is determined based on the pattern of markers in the second image. At the same time, a surface model of the phantom can be generated, using an optical surface imaging method. A third position of the phantom can be determined based on a comparison of the generated surface model and a reference surface model. The phantom can also be continuously monitored using an electromagnetic navigational system, such as a Calypso monitoring system, and a fourth position of the phantom can be determined based on the monitored position of the transponders embedded in the phantom. Based on the first, second, third, and fourth determined positions, a combined center for the phantom can be determined. The phantom, and ultimately the patient, can then be positioned at the combined center for the treatment system. A geometric parameter, such as, but not limited to, the treatment machine isocenter, and/or the uncertainty of each of these imaging and monitoring systems can also be determined based on the phantom positions determined using the different monitoring systems.

In an exemplary embodiment, the first imaging system can be a kV imaging system, such that the first image is a kV X-ray image, and the second imaging system is a kV imaging system, such that the second image is a kV X-ray image.

In another exemplary embodiment, the first imaging system can be a kV imaging system, such that the first image is a kV X-ray image, and the second imaging system is a MV imaging system, such that the second image is a MV X-ray image.

In another exemplary embodiment, the first imaging system can be a MV imaging system, such that the first image is a MV X-ray image, and the second imaging system is a MV imaging system, such that the second image is a MV X-ray image.

In another exemplary embodiment, the first imaging system can be a CT imaging system, such that the first image is a CT image, and the second imaging system is a CBCT imaging system, such that the second image is a CBCT image.

In another exemplary embodiment, a first imaging system is a kV X-ray imaging system, such that the first image is a kV X-ray image, and the second imaging system is a CBCT imaging system, such that the second image is a CBCT image.

In another exemplary embodiment, a first imaging system is a MV X-ray imaging system, such that the first image is a MV X-ray image, and the second imaging system is a CBCT imaging system, such that the second image is a CBCT image.

In other exemplary embodiments, the first imaging system can be any one of a kV, MV, CT, CBCT, MRI, SPECT, PET, ultrasound, or any other imaging system including molecular imaging, and the second imaging system can be any one of a kV, MV, CT, CBCT, MRI, SPECT, PET, ultrasound, or any other imaging system, including molecular imaging.

Any other combinations of imaging systems to obtain the first and second images, and ultimately the first and second phantom positions therefrom can be used. By using different imaging methods to obtain the first and second images, different shift values can be measured. Each of these imaging methods gives a slightly different position value. Therefore, by matching the images obtained using different imaging methods (i.e., kV-kV, MV-MV, kV-MV, MV-MV, CT-CBCT, kV-CBCT, MV-CBCT) different match values can be obtained, which then allows for detection of a systematic error in the treatment system/machine. Also, using the CT-CBCT match can produce a more accurate positioning result because there is more information in the CT and CBCT images obtained that can be used for the matching algorithms used to determine a geometric parameter of the radiation treatment system/machine.

Further, although only two images are presented as generated in the illustrative embodiment, any other number of images using different imaging systems can be used to provide an image-based position of the phantom.

It will be appreciated that the processes, systems, and sections described above can be implemented in hardware, hardware programmed by software, software instruction stored on a non-transitory computer readable medium or a combination of the above. For example, a method for can be implemented using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, end-to-end universal phantom for quality assurance using many imaging and verification modalities. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A method of calibrating a radiation treatment system with a single phantom based on a combination of phantom positions determined using a plurality of position monitoring methods, the method comprising:
    exposing the phantom to the plurality of position monitoring methods, the position monitoring methods comprising an imaged-based, an optical surface-based, and a navigational-based position monitoring method;
    determining a first position of the phantom in the radiation treatment system by exposing the phantom to the image-based position monitoring method;
    determining a second position of the phantom in the radiation treatment system by exposing the phantom to the optical surface-based position monitoring method;
    determining a third position of the phantom in the radiation treatment system by exposing the phantom to the navigational-based position monitoring method; and
    determining a combined center of the radiation treatment system based on a combination of the determined first, second, and third phantom positions, wherein the combined center is where a patient is to be positioned in the radiation treatment system prior to irradiation.

2. The method of claim 1,
    wherein the phantom includes a plurality of dose distribution measuring elements configured to provide dose distribution information of radiation dose delivered to the phantom, a plurality of position determining elements configured to provide position information of the dose distribution measuring elements relative to other elements of the phantom, and a plurality of markers including one or more transponders, wherein the determining of the plurality of positions comprises:

generating an image of the phantom using the imaged-based position monitoring, and determining the first position of the phantom based on a pattern of the plurality of position determining elements and the markers in the generated image;

generating a surface model of the phantom using the optical surface-based position monitoring, and determining the second position of the phantom based on a comparison between the generated surface model and a reference surface model; and tracking the positions of the transponders in the phantom using the navigational-based position monitoring method, and determining the third position of the phantom based on the tracked positions of the transponders.

3. The method of claim 1, wherein the phantom is exposed to the plurality of position monitoring methods simultaneously.

4. The method of claim 1, wherein the phantom is exposed to the plurality of position monitoring methods consecutively.

5. The method of claim 1, wherein the generating an image of the phantom using the imaged-based position monitoring includes generating one or more images of the phantom using an X-ray imaging system, an MRI system, a SPECT system, a PET system, a CT system, or an ultrasound imaging system.

6. The method of claim 1, wherein the generating a surface model of the phantom using the optical surface-based position monitoring includes generating a surface model of the phantom using one of a 3D laser imaging system or an ultrasound based scanning system.

7. The method of claim 1, wherein the tracking the positions of the transponders in the phantom using the navigational-based position monitoring method includes tracking the positions of the transponders using a Calypso monitoring system.

8. The method of claim 2, further comprising generating a second image of the phantom using a second imaged-based position monitoring, and determining a fourth position of the phantom based on a pattern of the plurality of position determining elements and the markers in the generated second image, wherein a calibrated position for the phantom in the radiation treatment system is determined based on the determined first, second, third, and fourth phantom positions.

9. The method of claim 8, wherein the first image is a kV X-ray image and the second image is a kV X-ray image.

10. The method of claim 8, wherein the first image is a kV X-ray image and the second image is a MV X-ray image.

11. The method of claim 8, wherein the first image is a MV X-ray image and the second image is a MV X-ray image.

12. The method of claim 2, wherein the plurality of dose distribution measuring elements includes one or more film inserts, and/or a dosimetric gel insert.

13. The method of claim 12, wherein the one or more film inserts includes a radiochromic film and/or thermoluminescent dosimeter film, and/or an optically stimulated dosimeter film.

14. The method of claim 12, wherein the plurality of dose distribution measuring elements includes two film inserts positioned in orthogonal planes.

15. The method of claim 8, further comprising determining a geometric parameter of the radiation treatment system based on the determined calibrated position for the phantom.

16. The method of claim 15, wherein the geometric parameter comprises one of an uncertainty of at least one a position monitoring system used for the plurality of position monitoring methods, a source-to-imager distance, a source-to-axis distance, an axis of rotation, a center of rotation, a piercing point, or an isocenter of the radiation treatment system.

17. The method of claim 8, further comprising determining a treatment position of a patient based on the determined calibrated position of the phantom.

18. The method of claim 1, wherein the phantom includes a combination of different dosimeters in a single dosimetric insert to thereby measure relative dose distribution and absolute dose distribution.

19. The method of claim 2, wherein the plurality of dose distribution measuring elements, the plurality of position determining elements, and the plurality of markers include different materials having different densities in order to provide substantially identical marker contrast in kV and MV images.

20. The method of claim 8, further comprising validating the radiation treatment system using the calibrated phantom position.

* * * * *